US012426785B2

(12) United States Patent
Hall et al.

(10) Patent No.: US 12,426,785 B2
(45) Date of Patent: Sep. 30, 2025

(54) METHOD AND SYSTEM FOR ASSESSING COGNITIVE FUNCTION OF AN INDIVIDUAL

(71) Applicants: Peter Anthony Hall, Waterloo (CA); Cassandra Lowe, London (CA)

(72) Inventors: Peter Anthony Hall, Waterloo (CA); Cassandra Lowe, London (CA)

(*) Notice: Subject to any disclaimer, the term of this patent is extended or adjusted under 35 U.S.C. 154(b) by 426 days.

(21) Appl. No.: 17/130,866

(22) Filed: Dec. 22, 2020

(65) Prior Publication Data

US 2021/0186330 A1 Jun. 24, 2021

Related U.S. Application Data

(60) Provisional application No. 62/995,299, filed on Jan. 24, 2020, provisional application No. 62/952,978, filed on Dec. 23, 2019.

(51) Int. Cl.
*A61B 5/00* (2006.01)
*A61B 5/055* (2006.01)
(Continued)

(52) U.S. Cl.
CPC .......... *A61B 5/0042* (2013.01); *A61B 5/0075* (2013.01); *A61B 5/4088* (2013.01);
(Continued)

(58) Field of Classification Search
CPC ... A61B 5/0042; A61B 5/0075; A61B 5/4088; A61B 5/6803; A61B 5/0073;
(Continued)

(56) References Cited

U.S. PATENT DOCUMENTS

| 2011/0137371 A1* | 6/2011 | Giftakis | A61B 5/293 |
| | | | 607/45 |
| 2011/0319700 A1* | 12/2011 | Schneider | A61N 2/02 |
| | | | 600/13 |

(Continued)

FOREIGN PATENT DOCUMENTS

CN 101500559 B * 1/2014 ............. A61K 31/00

OTHER PUBLICATIONS

Michela Balconi et al., "Repeated transcranial magnetic stimulation on dorsolateral prefrontal cortex improves performance in emotional memory retrieval as a function of level of anxiety and stimulus valence", Psychiatry and Clinical Neurosciences May 2013; 67: 210-218 (Year: 2013).*

(Continued)

*Primary Examiner* — Joel Lamprecht
(74) *Attorney, Agent, or Firm* — Shin Hung; VanTek IP LLP

(57) ABSTRACT

A method and system for assessment of cognitive function of an individual. The method includes having an individual execute a standardized cognitive task, followed by a brain perturbation which either excites or suppresses cognitive ability. The individual executes at least one further standardized cognitive task after the brain perturbation. Neuroimaging can be used concurrently while the individual is executing each of the tasks to obtain additional data to supplement the task scores. The post perturbation scores are compared against the pre-perturbation score to provide a standardized metric which can then be compared against individuals of the same gender and approximate age. These results can help predict and diagnose various brain diseases. A fitted helmet with integrated neuroimaging sensors, and with preset cutouts for receiving a TMS coil, facilitates positioning and (Continued)

orientation of the coil proximate the motor cortex and the dorsolateral prefrontal cortex for the above methods.

18 Claims, 12 Drawing Sheets

(51) Int. Cl.
  *A61B 5/377* (2021.01)
  *A61N 2/00* (2006.01)
  *A61N 2/02* (2006.01)

(52) U.S. Cl.
  CPC .......... *A61B 5/6803* (2013.01); *A61B 5/0073* (2013.01); *A61B 5/055* (2013.01); *A61B 5/377* (2021.01); *A61B 2560/0223* (2013.01); *A61N 2/006* (2013.01); *A61N 2/02* (2013.01)

(58) Field of Classification Search
  CPC . A61B 5/055; A61B 5/377; A61B 2560/0223; A61N 2/006; A61N 2/02
  See application file for complete search history.

(56) References Cited

U.S. PATENT DOCUMENTS

| | | | | |
|---|---|---|---|---|
| 2012/0130266 | A1* | 5/2012 | Mathan | A61B 5/313 600/544 |
| 2014/0303424 | A1* | 10/2014 | Glass | A61B 5/4094 600/9 |
| 2016/0235324 | A1* | 8/2016 | Mershin | A61B 5/6803 |
| 2021/0169417 | A1* | 6/2021 | Burton | A61B 5/4857 |

OTHER PUBLICATIONS

Michela Balconi et al., "Repeated transcranial magnetic stimulation on dorsolateral prefrontal cortex improves performance in emotional memory retrieval as a function of level of anxiety and stimulus valence", Psychiatry and Clinical Neurosciences May 2013; 67: 210-218 (Year: 2013) (Year: 2013).*

Yanmin Li et al., The effects of high-frequency rTMS over the left DLPFC on cognitive control in young healthy participants, Jun. 14, 2017 (Year: 2017).*

Kwon et. al., "Response Inhibition Induced in the Stop-signal Task by Transcranial Direct Current Stimulation of the Pre-supplementary Motor Area and Primary Sensorimotor Cortex", Apr. 14, 2013 (Year: 2013).*

Badran BW et al., Personalized TMS Helmets for Quick and Reliable TMS Administration outside of a Laboratory Setting, Brain Stimulation, https://doi.org/10.1016/j.brs.2020.01.009.

* cited by examiner

METHOD AND SYSTEM FOR ASSESSING COGNITIVE FUNCTION OF AN INDIVIDUAL

CROSS REFERENCE TO RELATED APPLICATIONS

This application claims the benefit of priority of U.S. Provisional Patent Application No. 62/952,978 filed on Dec. 23, 2019, and of U.S. Provisional Patent Application No. 62/995,299 filed on Jan. 24, 2020, which are hereby incorporated by reference.

FIELD

The present disclosure relates generally to testing and measuring cognitive ability of individuals.

BACKGROUND

Assessment of brain health normally takes place via the use of cognitive testing, self-reported symptoms or neuroimaging paradigms. In the case of the former, brain health is inferred via stronger performance on cognitive tests that assess an underlying cognitive ability of diagnostic interest; examples include standardized IQ tests, memory tests, and attentional tests. Some specific example cognitive tests include the Wechsler Adult Intelligence Scales and the Stroop Task.

With respect to self-reporting measures, these rely on reporting of symptoms that are salient to the patient themselves, including forgetfulness, concentration difficulties and the like. A specific example of a more structured form of self-reporting is the Mini-mental Status Exam.

Finally, neuroimaging technology is used to produce images of the brain over which certain parameters of brain function are laid. The functional parameters include electric signals and blood oxygenation changes that signify underlying neural activity, by example. Some specific neuroimaging examples include functional magnetic resonance imaging (fMRI), continuous wave near infrared spectroscopy (fNIRS), Electroencephalography (EEG) and diffuse optical tomography (DOT). Such neuroimaging systems can sense physical attributes in the brain.

There are some important parameters of brain do not require health for which there is no available assessment/diagnostic method. Cortical resilience is one such parameter. Cortical resilience refers to the ability of the brain to spring back efficiently from a perturbation (i.e., a suppressive force) of some kind. It is believed that cortical resilience can be assessed by applying a challenge function.

Within medicine, challenge functions—those that delivery a challenge to a target system and then assess the subsequent adaptation—are among the most commonly ordered tests in medicine around the world. For example, the oral glucose tolerance test, and the exercise stress test are two such challenge functions in common use today. These apply to the metabolic and cardiovascular systems, respectively. Such protocols are critical in diagnosing Type 2 diabetes and heart disease, two of the most lethal medical conditions in North America.

In the above examples of metabolic and cardiovascular systems assessment of resilience requires the application of a standardized perturbation, followed by assessment of the recovery of function, the latter occurring in a manner time lagged in relation to the original suppressive stimulus (perturbation). Despite widespread interest in the concept of "resilience" of whole organisms and bodily systems within organisms, there is no method for assessing it within the brain. The brain—especially the cortical regions involved in thinking, reasoning, inhibition and working memory—are especially sensitive to naturally occurring perturbations such as sleep deprivation, substance use, and stress. There are no prior known manners in which temporary perturbations could be introduced in a manner that allowed for assessment of resilience processes within the brain.

Another important parameter of brain health for which there is no available assessment/diagnostic method is cortical plasticity, or the ability of the cortex to adapt to a stimulus or exposure (environmental, developmental or otherwise).

Plasticity can be specifically understood to be positive or negative in valence. An example of positive plasticity is when a region of the brain becomes improved along functional or structural dimensions as a result of an exposure; for instance, physical exercise may increase the volume and functionality of the hippocampus in older adults. As such, exercise may be considered to induce (positive) plasticity in the hippocampus. Likewise, many substances of abuse induce decreases in functionality of the lateral prefrontal cortex (PFC), and these would be considered plasticity-inducing as well, but the valence of this plasticity would be negative (i.e., substance use results in decreases in functionality of the PFC, and loss of neuronal tissue).

Although magnetic resonance imaging (MRI) and functional MRI (fMRI) can be used to assess the above dimensions of plasticity—gain/loss of regional brain volume, the increase/decrease in functional activation—many aspects of plasticity refer to a latent capacity of the cortex that can only be revealed by introducing a performance-enhancing stimulus and observing the impact in real time. Yet many such stimuli are difficult to operationalize in a manner that could serve as a standardized diagnostic test.

Accordingly, there is a need for a system and method for quantifying human cortex performance, which in turn provides an indicator of brain health when compared to healthy baseline results of individuals of similar age and gender.

SUMMARY

It is an object of the present disclosure to obviate or mitigate at least one disadvantage of previous methods and systems for diagnosing and assessing brain health.

In a first aspect, the present disclosure provides a method for diagnosing and assessing cognitive function of an individual. The method includes executing by the individual in a pre-test calibration phase, a baseline cognitive interference task to determine a baseline performance parameter value for the individual; in a brain perturbation phase following the pre-test calibration phase, delivering brain stimulus at a calibrated level to the dorsolateral prefrontal cortex (dlPFC) of the individual by controlling a transcranial magnetic stimulation (TMS) coil that generates magnetic waves for changing a state of the brain during execution of the baseline cognitive interference task; executing by the individual in a cortical performance testing phase following the brain perturbation phase, at least one cognitive interference task of the same type as the baseline cognitive interference task to determine a corresponding at least one performance parameter value for the individual to complete the at least one cognitive interference task; and comparing each of the at least one performance parameter value to the baseline performance parameter value to provide at least one metric of brain health of the individual.

In this first aspect, the method further includes generating images of the brain with neuroimaging apparatus positioned on a head of the individual, while the individual executes the baseline cognitive interference task, and while the individual executes each of the at least one cognitive interference task.

In this first aspect, the calibrated level is determined in a baselining phase executed before the pre-test calibration phase, and includes calibrating a TMS stimulation intensity level for the individual. Here, calibrating the TMS stimulation intensity level includes determining a resting motor TMS threshold level for the individual, and setting the calibrated TMS stimulation intensity level between 70% to 90% of the resting motor TMS threshold level.

According to one embodiment of the first aspect, delivering brain stimulus includes controlling the TMS coil to deliver a magnetic field with a preset frequency, duration and magnitude corresponding to the calibrated TMS stimulation intensity level. The preset frequency, duration and magnitude are set to change the state of the brain into a suppressive state, or into an excitatory state.

In the embodiment where the brain is put into a suppressive state, in the cortical performance testing phase, the at least one cognitive interference task includes executing by the individual a first cortical test, a recovery period for the individual after completion of the first cortical test, and executing by the individual a second cortical test after the recovery period ends, the first cortical test, the second cortical test and the a baseline cognitive interference task being cognitive tests of the same type.

In this embodiment, TMS coil is controlled to deliver 600 pulses of stimulation continuously in a theta burst pattern including clusters of three 50 Hz pulses, repeated at 5 Hz. Then the first cortical test is executed 5 minutes after delivery of the brain stimulus has ended, the recovery period ends at 40 minutes after delivery of the brain stimulus has ended, and the second cortical test is executed immediately after the recovery period ends.

In an alternate embodiment, the TMS coil is controlled to deliver at least 300 pulses of stimulation continuously in a theta burst pattern including clusters of three 50 Hz pulses, repeated at 5 Hz. In this alternate embodiment, the first cortical test is executed 5 minutes after delivery of the brain stimulus has ended, the recovery period ends at 20 minutes after delivery of the brain stimulus has ended, and the second cortical test is executed immediately after the recovery period ends.

In the embodiment with the brain is put into an excitatory state, in the cortical performance testing phase, the at least one cognitive interference task includes a first plasticity test, a second plasticity test, a third plasticity test and a fourth plasticity test executed in sequence and indicating a transition between each test to the individual, where the first to fourth plasticity tests and the baseline cognitive interference task are cognitive tests of the same type.

In this particular embodiment, indicating the transition includes at least one of a minimally timed break and a display screen presenting each of the test changing color.

Alternately, the cortical performance testing phase further includes controlling the TMS coil to deliver a magnetic field to the dlPFC of the individual to change the state of the brain into a suppressive state after execution of the fourth plasticity test by the individual, executing by the individual a fifth plasticity test and a sixth plasticity test in sequence with a minimally timed break therebetween after completed delivery of the magnetic field, where the fifth plasticity test and the sixth plasticity test are cognitive tests of the same type as the first to fourth plasticity tests.

Alternately, the TMS coil is controlled to deliver 600 pulses of stimulation continuously in a theta burst pattern including triplet 50 Hz clusters of pulses repeating at 5 Hz, with a pattern of 2 seconds of active stimulation alternating with 8 seconds of delay, or the TMS coil is controlled to deliver 300 pulses of stimulation continuously in a theta burst pattern including triplet 50 Hz clusters of pulses repeating at 5 Hz, with a pattern of 2 seconds of active stimulation alternating with 8 seconds of delay.

In the embodiment where the brain is put into a suppressive state, in the cortical performance testing phase, the at least one cognitive interference task includes executing by the individual a first limit test, controlling the TMS coil to deliver a magnetic field to the dlPFC of the individual to change the state of the brain into an excitatory state after completion of the first limit test by the individual, and executing by the individual a second limit test after completed delivery of the magnetic field, where the first limit test, the second limit test and the baseline cognitive interference task are cognitive tests of the same type. In this embodiment, the TMS coil is controlled to deliver the magnetic field to change the state of the brain into an excitatory state any time between 3 hours and 24 hours after completion of the first limit test by the individual.

In a second aspect, the present disclosure provides a helmet for use in transcranial magnetic stimulation (TMS) operations. The helmet includes a body, adjustment means, a first TMS coil guide cut-out, a second TMS coil guide cut-out, and sensors. The body has an internal surface and an external surface, the internal surface being concave in shape and the external surface being convex in shape. The adjustment means is attached to the body for minimizing movement of the body when placed on a head of an individual. The first TMS coil guide cut-out extends from the external surface through to the internal surface, is shaped to receive and retain a correspondingly shaped TMS coil, and is positioned and oriented on the body for directing an inserted TMS coil generated magnetic wave to a motor cortex of the individual. The second TMS coil guide cut-out extends from the external surface through to the internal surface, is shaped to receive and retain a correspondingly shaped TMS coil, and is positioned and oriented on the body for directing an inserted TMS coil generated magnetic wave to a specific structure of the brain. The sensors are attached to the body and configured to detect levels of brain activity for neuroimaging.

In some embodiments of the second aspect, the specific structure is a dorsolateral prefrontal cortex (dlPFC).

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Generally, the present invention provides a protocol or method for assessment of brain health of an individual, using non-invasive brain stimulation, test runs executed by the individual and concurrent brain imaging during test execution. Specific embodiments will be described in relation to assessment of cortical resilience and cortical plasticity. Presently described method and system embodiments can further be used to quantify other parameters of the brain of an individual, such as lower and upper limits of their cognitive abilities. Furthermore, the testing methodology can be applied to other parts of the brain which can be subjected to non-invasive brain stimulation which can elicit a suppressing or stimulating effect which can be quantitatively measured with real-time brain imaging and/or standardized testing of the individual.

Figure 1:
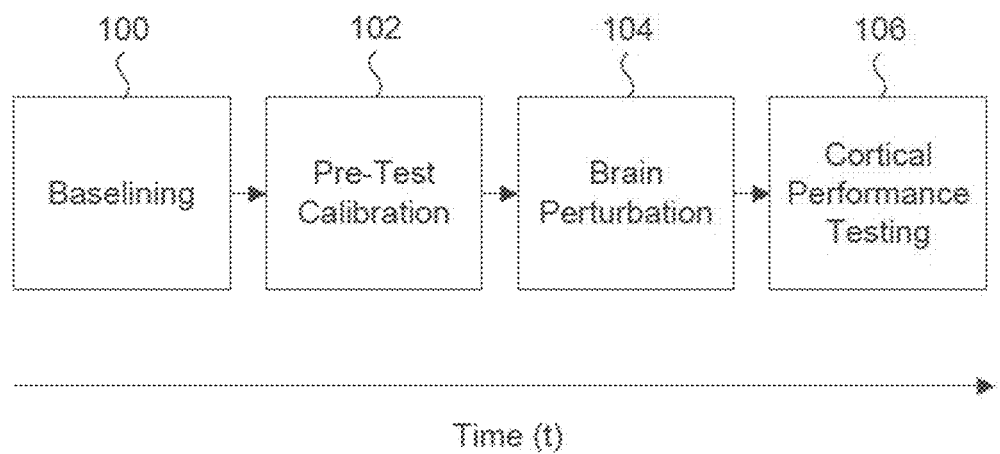
FIG. 1 is a block diagram showing a method for diagnosing and assessing brain health, according to a present embodiment.

FIG. 1 is a block diagram showing a method for diagnosing and assessing brain health, according to a present embodiment. As will be described later, this generic method is applicable for the specific embodiments relating to cortical challenge, cortical plasticity and limited testing.

In FIG. 1 are a sequence of four phases that are executed in the sequence shown from left to right. These phases are a Baselining phase 100, a Pre-Test Calibration phase 102, a Brain Perturbation phase 104, and a Cortical Performance Testing phase 106. A time vector having a scale which can be in seconds, minutes or days shows the direction of passage of time. In other words, phase 100 is executed before phase 102 in time, and so forth. Each phase 100, 102, 104 and 106 can have one or more steps and actions that are taken to achieve the objectives of that respective phase.

It is noted that depending on the specific type of testing being done, breaks in time between each of the phases can be taken where the individual under test is not subjected to any testing activity and can rest. The time and frequency of the breaks will depend on the type of test being conducted, and some breaks can occur within the phases themselves. The overall purpose and function of the phases shown in FIG. 1 are now described.

The Baselining phase 100 is used to determine the lower threshold of intensity of stimulation that is required to elicit a change in cortical response in the individual under test. Hence, this can be considered a physiological baseline evaluation phase. Individual baseline cortical responsivity is unique and variable to each individual. It has been observed that the baselining results can change over extend time between sittings/sessions, therefore baselining is performed for each new sitting by the individual when brain perturbation is to be administered. This lower threshold is used later in the following Brain Perturbation phase 104, which is described later. This Baselining phase 100 involves use of a transcranial magnetic stimulation (TMS) coil appropriately positioned on the head of an individual under test, which is computer controlled to deliver changing levels of stimulation in iterative steps, where each iteration observes feedback from the individual until some predetermined threshold is met.

The positioning of the TMS coil can depend on the type and location of physical response exhibited by the individual which is to be observed as the stimulation changes with each iteration. Therefore the lower threshold corresponds to a specific magnitude of the field generated by the TMS coil. By example, the TMS coil can be positioned and directed to the part of the brain that elicits a twitch of the toe. Any neuroelectric signatures of response, such as a motor evoked potential (MEP), or visual artefacts (phosphenes) can be observed. The latter could be used if the calibration was accomplished by applying the pulses to the visual areas of the cortex instead of the motor cortex.

Persons skilled in the art will understand that a TMS coil is controlled to generate a magnetic field as a single or series of multiple repetitive pulses. Multiple repetitive pulses are referred to as rTMS.

It should be noted that a higher magnitude or intensity of magnetic field than the lower threshold can be used. However, the lower threshold level is considered safer or the individual under test as the lower threshold avoids the potential for triggering "overstimulation syndrome", or a seizure which can occur if the magnitude of the magnetic field is too high.

The Pre-Test Calibration phase 102 is another form of baseline testing to determine brain performance of the individual in the absence of any brain stimulus being applied. This tests the normal cognitive capability of the individual. During this phase, the individual must complete specific tasks, which are standardized or well known in the art. Hence, this can be considered the performance evaluation of the individual in response to a specific type of test. The individual is scored based on their responses, and brain imaging sensor devices can be used concurrently to record activity in the individual's brain as they respond to the task. This baseline data can then be used later on for comparison against the later Cortical Performance Testing phase 106.

The Brain Perturbation phase 104 is the application of brain stimulus, which can be excitatory or suppressive in nature, to artificially change the state of the brain during which the Pre-Test Calibration phase 102 is executed. This phase applies brain stimulus via the TMS coil positioned over a certain area of the brain. The TMS coil can be controlled to deliver the magnetic field with a preset frequency, duration and magnitude. In one embodiment, the magnitude of the field is set based on the lower threshold determined in the previous Baselining phase 100. This lower threshold would be used for both the excitatory and suppressive forms of brain stimulation.

Once the Brain Perturbation phase 104 has been completed, to either excite or suppress cortical activity, the Cortical Performance Testing phase 106 can then begin. The Cortical Performance testing phase 106 includes one or more cognitive tests, and in some embodiments additional brain perturbation, for the purposes of obtaining some measure of brain performance of the individual in response to the initial Brain Perturbation phase 104.

In the Cortical Performance Testing phase 106, at least one test similar in type to the one administered in the Pre-Test Calibration phase 102 is executed by the individual under test. The purpose of this phase is to assess the performance of the individual in response to specific tests while their brain is under an artificially induced state that they would otherwise not be normally functioning under.

Similar to the pre-test calibration phase 102, brain imaging can be used to capture some physical attribute of the brain as the test is being executed by the individual. Any test scores/values completed by the individual and the brain imaging results can be used in comparison to baseline test scores/values obtained in the Pre-Test Calibration phase 102. Multiple tests can be conducted in the Cortical Performance Testing phase 106, which may be conducted over a period of time to provide additional information about the health of the individuals' brain as a function of time. This phase can also include further brain perturbation. The test results can then be compared against a normative value from an existing age and sex stratified database in order to obtain a percentile, much like a standardized IQ score. Other databases can include standardized values for specific medical populations.

In an embodiment where the test method of FIG. 1 includes a suppressive type of brain perturbation, then the test results can advantageously assist with the early detection and subsequent diagnosis of disorders that affect the cortical functions in an insidious manner, such as dementia, diabetes, and depression by example.

In an alternate embodiment where the test method of FIG. 1 includes an excitatory type of brain perturbation, then the test results can advantageously assist with detecting loss of cortical plasticity, and in particular positive plasticity. While not an exhaustive list, this can help detect diseases such as Alzheimer's, Parkinson's and Stroke by example.

Cortical resilience is defined as the ability of the cortex to recover efficiently from transient perturbation. There is good reason to believe that prevalent medical conditions affecting the brain may leave neural traces in resilience parameters that show up years before formal diagnosis, based on prior studies using traditional instruments. Examples of such traditional instruments include self-report symptoms for mild cognitive impairment, and cognitive testing for Alzheimer's and other dementias. One of the main problems with psychiatric symptomology is that it is measured by self-reporting by the afflicted individual. It should be apparent to those skilled in the art that the accuracy, bias and subjectivity of such self-reporting does not result in consistently usable data.

Despite widespread interest in the concept of resilience—the ability to spring back (recover) from a temporary perturbation—there are no brain health metrics that measure it directly. Current methods for assessing brain health involve inferred neuronal activity via changes in electrical fields or signs of regional oxygenation changes in brain tissues. These parameters are typically measured at rest, during performance of a cognitive task or both. More commonly, brain health is inferred via cognitive task performance itself, without functional imaging. None of these strategies assess "recovery from perturbation," which is the crux of the resilience construct when referencing the brain or any other bodily system all. Assessing both aspects of the resilience definition are necessary: the induction of a perturbation (standardized), and the careful assessment of time course of recovery. There are no adequate measures of cortical resilience currently available.

In the following embodiment, the proposed method and system detects the presence of underlying (but subjectively asymptomatic) abnormal brain function parameters that predict future occurrence of disorders affecting the human brain (e.g., dementias, type 2 diabetes, concussion). The early detection of these functional abnormalities may facilitate earlier and more successful preventative interventions for diseases such as dementia, type 2 diabetes and concussion by example.

Figure 2A:
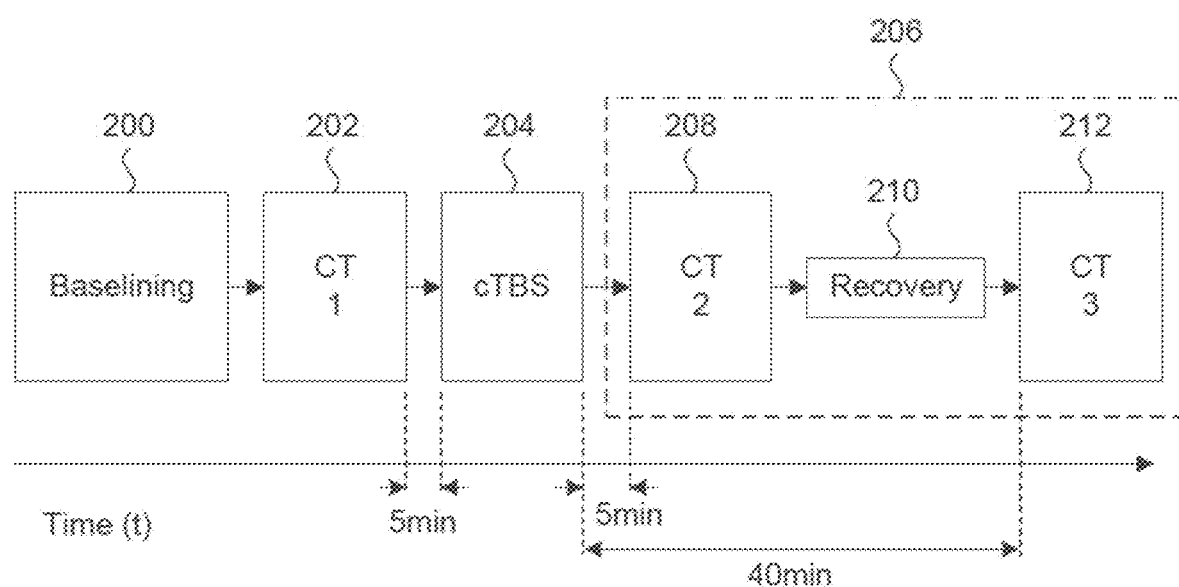
FIG. 2A is an alternate embodiment of the method of FIG. 1 showing a method for testing cortical resilience (CCaRT)

Following is a discussion of an embodiment of the test method of FIG. 1 that specifically tests the level of cortical resilience of an individual, with reference to FIG. 2A. This is referred to as the Cortical Challenge and Recovery Test (CCaRT). In the embodiment shown in FIG. 2A, a suppressive type of brain perturbation referred to as continuous data burst stimulation (cTBS) is used. cTBS is a variant of rTMS that induces a transient state of decreased excitability in targeted neuron populations within the human cortex; the specific cortical region targeted is the dorsolateral prefrontal cortex (dlPFC), a region involved in decision-making, working memory, inhibition, and mental flexibility. Cortical response is assessed by a combination of cognitive testing and functional brain imaging.

A principle of the CCaRT embodiment is the use of cTBS to induce a temporary state of decreased excitability (suppression) in targeted neuronal populations in the neocortex of the human brain, specifically in the left dorsolateral prefrontal cortex; dlPFC. The usual time course for the rTMS suppressive effect is approximately 30-40 minutes; slightly faster and slower recovery can be interpreted as a resilience metric (i.e., more or less cognitive resilience, respectively). This suppressive effect is quantified by cognitive testing and continuous wave near infrared spectroscopy (fNIRS), or similar brain imaging system metric.

In FIG. 2A are a sequence of four phases that are executed in the sequence shown from left to right, which generally correspond to the four phases shown and described in FIG. 1. A time vector having a scale which can be in seconds, minutes or days shows the direction of passage of time. These phases are a Baselining phase 200, an initial Cortical Test 1 baseline phase 202 (CT1), a Cortical Suppression (cTBS) phase 204, and a Performance Test phase 206.

The Baselining phase 200 corresponds to the Baselining phase 100 in FIG. 1. The initial Cortical Test baseline phase 202 corresponds to the Pretest Calibration phase 102 of FIG. 1. The Cortical Suppression phase 204 corresponds to the Brain Perturbation phase 104 of FIG. 1. The Performance Test phase 206 corresponds to the Cortical Performance Testing phase 106 of FIG. 1. In the present embodiment, the Performance Test phase 206 includes 3 sub-phases: a second Cortical Test 2 sub-phase 208 (CT2) followed by a Recovery sub-phase 210 of predetermined time length, and a final Cortical Test 3 sub-phase 212 (CT3).

Generally speaking, changes in the individual response from CT1 to CT2 quantify the initial suppressive effect of the cTBS perturbation. The individual response from CT3 provides an index of recovery, expressed as a proportion of the initial suppression effect recovered at time-lagged post stimulation (the usual time when the suppressive effect wears off). Now the phases and the sub-phases of FIG. 2A are now described in further detail in the context of the cortical resilience test method flowchart of FIG. 2B.

In the Baselining phase 200, a resting motor threshold of the individual is first determined at 300. This can be any standard procedure to determine resting motor threshold. In the present embodiment the TMS coil is positioned proximate to the motor cortex, where the machine delivers one magnetic pulse at a time, targeting a brain region that controls movement (motor cortex) in the thumb. Following is an example of how this is done. Starting at 40% of the TMS machine maximum, single biphasic stimulation pulses in sets of 10 are delivered, each separated by 3 seconds using either observable thumb twitch or 50mv deflection of motor evoked potential as a "hit" criterion. The stimulation intensity is continually adjusted upward in 2% increments until 5/10 pulses result in a response that qualifies as a "hit.".

Starting low and moving upward by 2% stimulation intensity increments results in a gradual increase in the proportion of hits (thumb twitches) per pulses delivered. In this specific example, the machine is controlled to continue administering individual pulses in batches of 10, until the number of hits (pulses resulting in a twitch) reaches 5/10. This intensity value of the TMS coil when this threshold is met is taken as the lower threshold of what intensity of stimulation is required to result in a change in cortical response. This is a required first step for almost all TMS protocols to ensure that the stimulation level is customized to individual baseline cortical responsivity, given that the latter is quite variable. Those skilled in the art will understand that other sequences with varying time steps voltage steps and "hit" thresholds can be used to achieve the same desired result.

Still in the Baselining phase 200, in the next step 302, the cTBS stimulation value is set. cTBS is a suppressive variant of rTMS which introduces a standardized perturbation to the human cortex. In the present embodiment, this is calculated as 80% of this absolute numerical value of the final stimulation intensity value resulting from step 300 to set as the stimulation intensity of the TMS coil going forward for all subsequent steps. While 80% is selected in this embodiment, the value can be set at 90%, 100% or 110%, but 80% is the lowest threshold that reliably induces changes in cortical excitability. Lowest possible values are generally desired in order to make the procedure as safe as possible, by avoiding the potential for triggering "overstimulation syndrome", or a seizure. This now ends the Baselining phase 200.

CT1 includes step 304 for administering a baseline interference task. Such interference tasks are well known in the art, and include by example Stroop, Flanker and MSIT (Multi Source Interference Task). This task is coupled with functional activation quantification. Functional activation quantification can include having the individual actuate a keyboard or a handheld device, such as one that includes a simple button by example, which is registered and recorded. Any type of feedback mechanism triggered by the individual under test can be used. In a variant of this embodiment, brain imaging is recorded during the task to complement the feedback response data. More specifically, functional activation changes can be quantified by functional brain imaging using the system such as fNIRS covering the medial and lateral regions of the prefrontal cortex. As previously mentioned, other brain imaging systems can be used in place of fNIRS or in conjunction with each other if possible.

Delay time for responding to the cognitive task is one measurable parameter that is used. This delay time is considered the normal cognitive response time for the individual. This delay time obtained after the interference task is completed by the individual is given a score based on the type of interference task that is administered and is now referred to as the Baseline Task Score.

Next at step 306 is to localize the dorsolateral prefrontal cortex (dlPFC). This can be done using a standardized method such as neuronavigation or Beam F3 by example, to localize the dlPFC, or other targeted region which is to be subjected to the brain perturbation by the TMS coil. The localization should be completed within the 5-minute time window following the completion of the prior baseline cognitive task in step 304. A longer time window is permitted but at the cost of an earlier part of the time series data curve. This cognitive task can be brief, such as the Multi Source Interference Task (MSIT) by Bush & Shin, 2006, Nature Protocols. This example 5 minute time window is shown in FIG. 2A between the phases 202 and 204. Once localized, the TMS coil can be properly positioned on the head of the individual. Any type of apparatus can be used secure the TMS coil in position.

In the present embodiment, step 306 is included as part of CT1 to end the phase. Alternately, step 306 can be included as part of the Cortical Suppression phase 204 to begin its phase.

Next is the Cortical Suppression phase 204 that includes step 308, which is delivery of stimulation by the TMS coil which has been previously positioned on the head of the individual at step 306. At 5 minutes post task conclusion (step 304), the positioned TMS coil is controlled to deliver 600 pulses of stimulation continuously in the theta burst pattern: clusters of three 50 Hz pulses, repeated at 5 Hz. This is referred to as continuous theta burst stimulation (cTBS). Here, the burst (or cluster) of three 50 Hz pulses is rTMS. Hence cTBS in the presently described embodiment includes bursts of rTMS.

It should be noted at the present time the primary use of Repetitive Transcranial Magnetic Stimulation (rTMS) is therapeutic, rather than for diagnostic purposes. The therapeutic use of rTMS usually involves excitatory stimulation rather than suppressive stimulation, and is administered in many daily sessions for several weeks in order to achieve lasting therapeutic benefit (in treatment of depression, for example). This represents about 95% of the clinical usage of TMS. Suppressive stimulation of the type described in the present cortical suppression embodiments (continuous theta burst stimulation; cTBS), is not routinely used in therapeutic use of rTMS, and has not previously been used for diagnostic or prognostic purposes.

The primary current use of cTBS is in experimental brain research, as a means for inducing a transient "virtual lesion", in order to facilitate mapping of the function of brain systems (i.e., to identify where different functions are localized in the neocortex). The proposed use of cTBS in the present embodiments for diagnosing cortical resilience involves combining knowledge of the absolute causal effect of this specific suppressive variant of rTMS with timeline for its reversal to operationalize the concept of cortical resilience, and to quantify individual values of cortical resilience for those undergoing the assessment. One variant of TMS (not rTMS) that has been used in assessment contexts is the use of single (not repeated) pulses of magnetic stimulation to assess speed of motor conductivity (central vs peripheral nervous system). Another variant uses pairs of pulses ("paired pulse paradigms") to show priming of single pulse effects on brain circuits. Neither of these two latter applications of single pulse effects overlap with the cTBS protocol (a multiple pulse train) employed the present embodiments, and neither is routinely used for diagnosis of prognostic purposes.

After the cTBS stimulation has terminated to end the Cortical Suppression phase 204, the individual under test is given a break of 5 minutes when no testing activity is administered. The individual is simply allowed to rest. This 5 minute break is shown in FIG. 2A between the end of the Cortical Suppression phase 204 and the beginning of CT2.

At the end of the 5 minute break begins the Performance Test phase 206. The first sub-phase is CT2 which is to have the individual complete a second interference task, which corresponds to step 310 in FIG. 2B, and this second interference task is the same type of task as the one administered in step 304. For example, different set of Stroop tasks are used in CT1 and CT2. Again similar to CT1, the response data and any brain imaging data from the individual under test is registered and scored. This is now referred to as the Post Perturbation Task Score.

After the individual has completed the second interference task to end CT2, the individual is given another break shown as recovery sub-phase 210. Regardless of the time taken for completing CT2, the recovery time ends at 40 min timed from the end of the Cortical Suppression phase 204. This 40 minute time-locked period from the end of the Cortical Suppression phase 204 is shown in FIG. 2A. It should be noted that all times shown in FIG. 2A are not to scale.

It is assumed that the individual will score worse in the CT2 than in the initial CT1 due to the cTBS stimulation. More specifically the individual should exhibit more delay in responding to the tasks after the cTBS cortical suppression. Therefore, a perturbation effect of the cTBS can be calculated as the Baseline Task Score minus the Post Perturbation Task Score, with this difference expressed as a percentage of the Baseline Task Score:

(Baseline Task Score−Post Perturbation Task Score)/
Baseline Task Score

At the end of the 40 min period after cTBS Cortical Suppression phase 204, CT3 begins. Returning to the flowchart of FIG. 2B, this corresponds to step 312 where a final interference task is executed. Again, this final interference task is of the same type as the ones administered in steps 304 and 310. The resulting data is converted into a score, which is now referred to as the Recovery Task Score. It should be understood that specific test given to the individual in each of CT1, CT2 and CT3 are not identical in the detailed tasks or questions being asked, but are each still structured or configured in the same way.

Figure 2B:
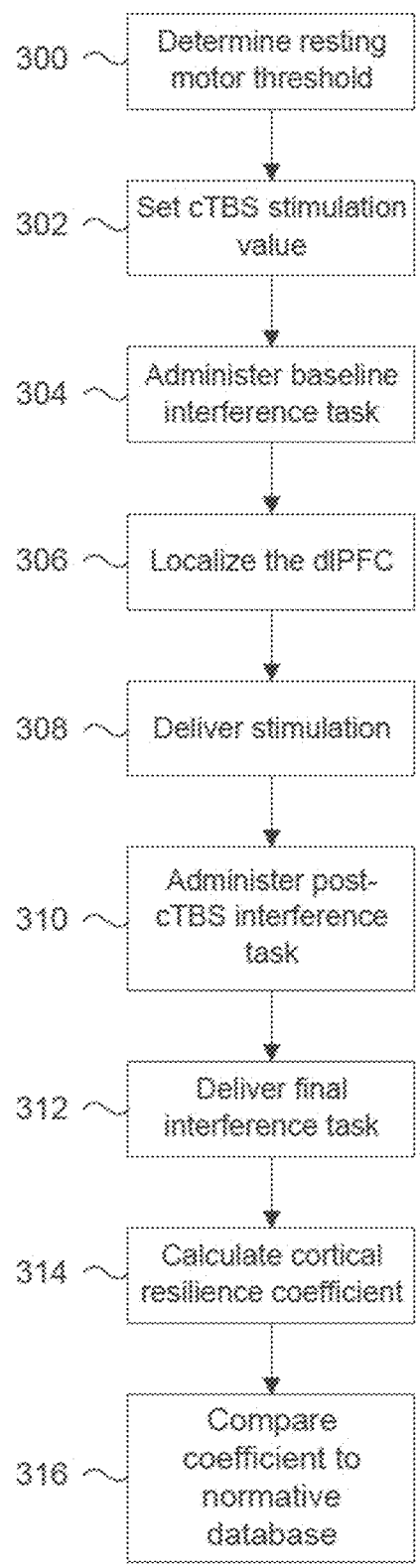
FIG. 2B is a flow chart summarizing the method steps of the CCaRT protocol shown in FIG. 2A, according to a present embodiment.

The final steps 314 and 316 of FIG. 2B can be executed any time after CT3 ends. Now having the Recovery Task Score, the Baseline Task Score and the Post Perturbation Task Score, the Cortical Resilience Coefficient can be calculated at step 314. This is done by calculating the proportion of the decrement (in task performance and functional activation parameter) recovered by the final cortical response measurement. More specifically, this is the proportion of the difference between the response from step 304 (Baseline Task Score) and the response from step 310 (Post Perturbation Task Score produced by cTBS), that has dissipated by the response from step 312 (Recovery Task Score). This value reflects the metric of cortical resilience, with higher values indicating higher cortical resilience.

Finally at step 316, this cortical resilience coefficient can then be compared to normative values from an existing age and sex stratified database. This comparison with the database will provide an indication of the brain health of the individual under test.

With respect to the brain imaging, the brain imaging data can also be used in the same way. In the present example embodiment where fNIRS is used, sensors can be applied easily proximate to the prefrontal cortex of the individual and left in place prior to and following stimulation. In this way, cognitive perturbation magnitude and recovery can be approximated by changes in concentration of oxygenated hemoglobin (OxyHb), deoxyhemoglobin (DeOxyHb) and/or total hemoglobin (TotHb), within defined regions of interest within the cortex (e.g., dlPFC). The specific metric (OxyHb, DeOxyHb, TotHb) and channel of measurement (corresponding to the dlPFC or otherwise) may then be used to quantify subsequent cortical resilience parameters, separately or in combination. Therefore, this resulting brain imaging data can also be compared against normative brain image data from the existing age and sex stratified database in order to obtain a percentile, much like a standardized IQ score. Other examples of brain imaging systems include EEG, fMRI and DOT, which can be used in place of or in conjunction with fNIRS. This listing is not exhaustive, and any new brain imaging technology can be employed in the presently described embodiments.

Accordingly, quantification of initial suppression effects and subsequent recovery effects can be quantified in a number of ways, including cognitive test score changes and functional activation changes as detected from concurrent brain imaging during the testing, whether it be from one or more different brain imaging systems.

Figure 2C:
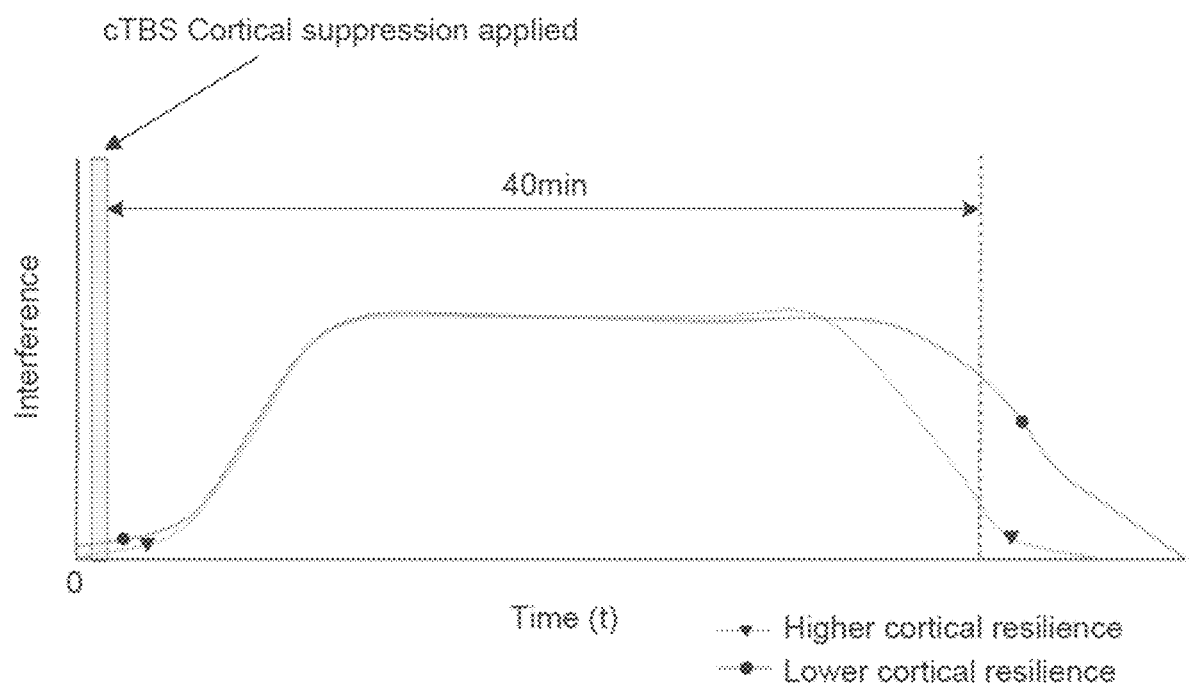
FIG. 2C is a graph plotting example comparative results of the test from FIG. 2A between individuals with higher and lower cortical resilience.

FIG. 2C is a graph showing the example time course of the initial suppressive effect of cTBS, followed by the expected time course of the recovery effect for two individuals who have undergone the CCaRT shown and described in FIG. 2A and FIG. 2B. The line shown with a triangle annotation represents data for an individual with higher cortical resilience, whereas the line shown with a circle annotation represents data for an individual with lower cortical resilience. Both curves are smoothed time series data. The horizontal axis is time, and the vertical axis is the degree of cortical suppression when a higher value indicates higher interference suffered by the individual. The units depend on the specific test used, or brain imaging metric. FIG. 2C illustrates on the left-hand side delivery of the cTBS stimulation as would occur in the Cortical Suppression phase 204 of FIG. 2A. The level of interference experienced by the 2 individuals gradually increases over time after cTBS stimulation has ended, eventually hitting a plateau. The 40 minute time period beginning at the end of the cTBS stimulation delivery is also illustrated. In this particular example, although there is no testing being conducted in the Recovery phase 210, the plot can interpolate the plateau from the data obtained in CT2 and CT3.

As time approaches the 40 minute mark, it can be seen that the line with the circle annotation remains fairly high. This indicates that this individual still suffers from the effects of the earlier cortical suppression. In contrast, the line with the triangle annotation has dropped significantly at the 40 minute mark, indicating that this individual only suffers from residual effects of the earlier cortical suppression.

Accordingly, by tracking the rate of dissipation of an induced state of inhibition using changes in cortical excitability over the expected time window of the stimulation effect, cortical resilience can be quantified on the individual level. Those with quicker recovery times (see FIG. 2C line with triangle annotation) for a given level of inhibitory stimulation would reasonably be classified as demonstrating more cognitive resilience than those with a longer recovery time (see FIG. 2C line with circle annotation), assuming that the stimulation is adjusted to individual baseline differences in resting or active motor threshold.

In the previously described embodiment of the Cortical Challenge and Recovery Test (CCaRT), the Cortical Suppression phase 204 of FIG. 2A the TMS coil is controlled to deliver 600 pulses of stimulation continuously in the theta burst pattern: clusters of three 50 Hz pulses, repeated at 5 Hz. For simplicity, this is referred to as cTBS-600, but also requires the fairly long Recovery phase 210 that ends 40 minutes after cTBS stimulation delivery.

According to an alternate embodiment of CCaRT, referred to as Mini-CCaRT, the total administration time is significantly reduced to about one half the time. In this alternate embodiment of Mini-CCaRT the TMS coil is controlled to deliver 300 pulses at the same frequencies instead of 600 pulses in cTBS-600. As a result, CT2 with the Recovery phase 210 time for completion after cTBS stimulation is reduced to 20 minutes before the start of CT3. Therefore the total time to administer Mini-CCaRT is quicker than CCaRT, severity and remission status of symptoms of a variety of psychiatric symptoms that adversely affect prefrontal cortex (PFC) function, including depressive disorders and post-traumatic stress disorder, without reliance on self-reporting.

The proposed method embodiment of FIG. 2A enables tracking of changes in brain health over time, both in clinical contexts for tracking changes in brain health as a function of age, treatments, etc., and in research contexts whereby example brain health outcomes in clinical trials and longitudinal studies of brain health are assessed.

The proposed method embodiment of FIG. 2A can be used to identify individuals who may be especially susceptible or resistant to occupational/environmental conditions that perturb the function of the prefrontal cortex. These include by example sleep deprivation, neurotoxic substances, acute stress, and strong emotional stimuli. Hence one application of the embodiment is to assist in selecting personnel and filtering out personnel for specific jobs where such conditions may be occasionally present or pervasive.

The example clinical and research categories of application for the previously described CCaRT embodiment are summarized in Table 1 below:

TABLE 1

| | Context | | | | |
|---|---|---|---|---|---|
| | Clinical | | | Research | |
| | | | | Randomized | Longitudinal studies |
| | Diagnosis | Treatment progress/outcome | Experimental | trials (outcomes) | (population brain health metric) |
| | Disease conditions | | | | |
| Chronic disease conditions (diabetes, obesity) | X | X | X | X | X |
| Neurodegenerative disease (MCI, Alzheimer's, FTD) | X | X | X | X | X |
| Brain injury (TBI, concussion) | X | X | X | X | X |
| Addictions, Depression and other Psychiatric Disorders | X | X | X | X | X |
| | Normative development | | | | |
| Age-related cognitive change over the lifespan | | | | X | X |
| Emergence of cognitive capacities | | | | X | X |
| Lifestyle behaviors (eating, exercise, sleep) | | | X | X | X |

Note:
MCI = Mild Cognitive Impairment; FTD = Frontotemporal Dementia; TBI = Traumatic Brain Injury. As a brain health metric, the CCaRT paradigm can be used for research paradigms wherein the brain is serving as an outcome, predictor, mediator and/or moderator.

although CCaRT is more suited for diagnostic purposes. The selected number of 600 or 300 pulses for cTBS have been previously demonstrated to have effective suppressiveness. cTBS-600 is more robust and provides a better suppressive effect on the individual. In the future, different apparatus with corresponding parameters can be used to provide the desired suppressive effect.

The previously described CCaRT and Mini-CCaRT embodiments utilize cTBS to suppress cortical functions for the purposes of diagnosing or testing for cortical resilience of an individual. More specifically by example, the previously described method embodiments can be used to track Future advancements in technology may allow for the integration of new modes of brain imaging into the cortical response measurement facet of the method, or to combine several existing brain imaging modalities (fNIRS+EEG), or to use a completely new type of imaging system, such as DOT by example. It is also likely that new stimulation parameters could be employed to induce suppressive effects on a more rapid time scale, thereby reducing the total time for the method. One current example is the Mini-CCaRT method mentioned above, which will reduce the total time to 25 minutes. This could be reduced further with new rTMS methods.

Finally, further refinement in equipment for delivery of the method will make the integration of the cortical response measurements and the TMS stimulation delivery to be more "turnkey" with little input from the operator. The latter may be particularly useful in clinical settings that rely on efficiency and delegation of diagnostic assessment procedures, and research settings that require short measurement completion times. Finally, the application of machine learning paradigms will allow for the extraction of maximally predictive/diagnostic parameters from the CCaRT method, for any of the above specific clinical or research applications. Such approaches could identify time points, measurement channels, or data combination functions that predict the standard resilience metric (and yet can only be derived from CCaRT).

The CCaRT embodiments provides a completely new category of brain health parameter to facilitate prognosis, diagnosis, personnel selection and research activities. Pending additional validation processes, this new method may augment or possibly replace existing diagnostic procedures, which currently still rely on symptom reporting or cognitive testing in isolation. Diagnostic accuracy will increase, particularly for the most common forms of dementia (Alzheimer's dementia, frontotemporal dementia). Personnel selection is almost entirely based on interview and self-report data, with very little use of even cognitive testing: The CCaRT embodiments assesses one very important facet of mental suitability for extreme environments that may not be easily assessed otherwise (i.e., the capacity to remain unaffected by sleep deprivation, strong emotional stimuli, neurotoxins, stress or other sources of cognitive perturbation). At minimum, the CCaRT embodiments will provide a new set of cognitive parameters from which to predict job success that have no overlap with any existing parameter (even current cognitive tests). Finally, the building of large normative data bases of CCaRT data may allow for increasingly precise estimates of risk, diagnostic probability and other important parameters for clinicians.

The previously described method and system embodiments assist with the early detection and subsequent diagnosis of disorders that affect the cortical functions in an insidious manner (e.g., dementias, diabetes, depression), without the use of self-report with its associated biases. The method and system embodiments have many applications within the medical domain as a diagnostic procedure, a method to track symptom change over time (e.g., as a function of the natural course of a disease process, or in response to treatment efforts), as well as outcome assessment in clinical research trials and longitudinal studies of brain health. A final potential application is within personnel selection, as a method for identifying individuals who are particularly immune to (or sensitive to) natural perturbations that may exist in the workplace in extreme work environments (e.g., pilots, military personnel, first responders, physicians, nurses).

The previously described embodiments are not limited to PFC applications, and could also be applied to other areas of the cortex.

In alternate embodiments of the method for diagnosing and assessing brain health shown in FIG. 1, cortical plasticity can be diagnosed and tested in individuals.

It is possible to observe excitatory effects of brain stimulation on the brain, using rTMS. Several types of rTMS can introduce enhanced excitability and functionality of focal regions of the neocortex of the brain, particularly when targeting the PFC. One stimulation variant, known as intermittent theta burst stimulation (iTBS), can do so with high efficiency. The iTBS protocol involves 50 Hz triplet pulses introduced at 5 Hz for 2 seconds continuously, followed by an 8 second gap, continuing for a total of 600 pulses (approximately 3 minutes). This produces an enhanced state of excitation in the targeted PFC cortex for up to 30 minutes.

This is referred to as iTBS-600. Alternately, a shorter version called iTBS-300 can be used where the difference over iTBS-600 is that iTBS-300 uses a total of 300 pulses instead of 600. Excitatory effects are provided by iTBS-300, but are more robust and the excitatory effects are more pronounced with iTBS-600.

Many brain disorders and the aging process may introduce loss of "positive" plasticity, and this loss of plasticity may have diagnostic significance. The use of a plasticity metric involving iTBS therefore serves as a way of quantifying plasticity loss early in the diseases process. Although most may respond to iTBS with enhanced cortical excitation, there are many individual differences, and such differences may reflect underlying characteristics of the cortical tissues that map clearly onto the concept of plasticity.

The following embodiments describe a method for assessing an individual's likelihood of responding positively to interventions that are intended to augment prefrontal function, for example via exercise, brain stimulation or computer based cognitive training. The parameters generated from the test can also have various clinical diagnostic utilities, such as detecting the presence of insidious brain pathology. For example, pathologies that affect brain plasticity, such as dementia.

The proposed protocol involves tracking changes in brain response to a standardized excitatory stimulation, following an initial suppressive stimulation. The excitatory stimulation is delivered by intermittent theta-burst stimulation (iTBS).

Figure 3A:
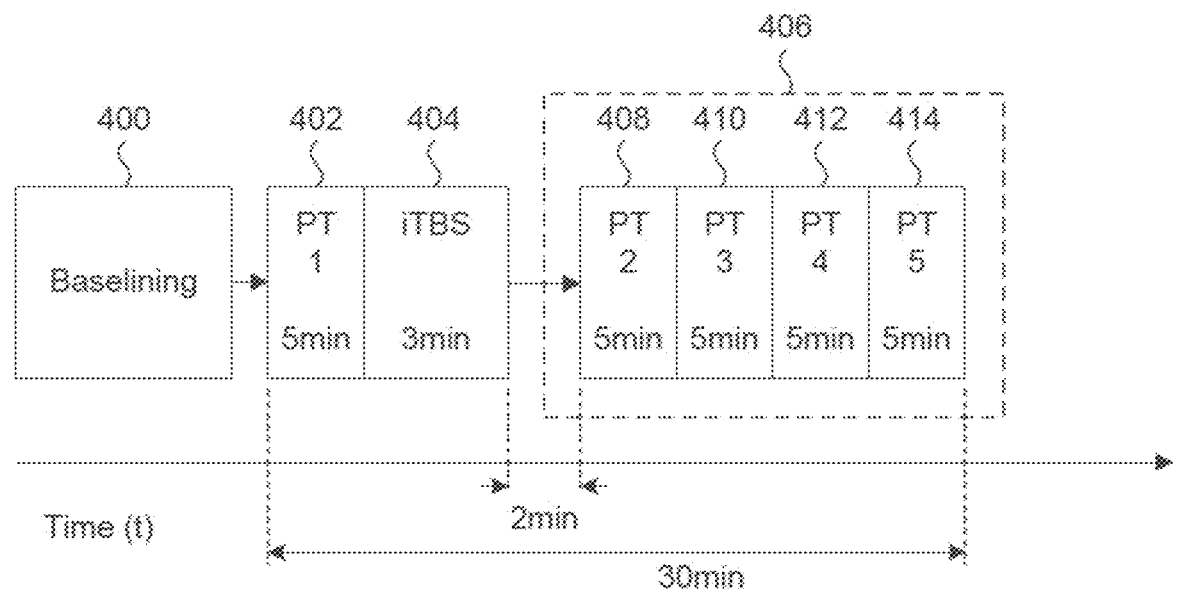
FIG. 3A is an alternate embodiment of the method of FIG. 1 showing a method for testing cortical plasticity, according to a present embodiment.

Reference is now made to FIG. 3A which is an alternate embodiment of the method of FIG. 1 showing a method embodiment for testing cortical plasticity, referred to as the Unidirectional Cortical Plasticity Test (CPT-1D). CPT-1D is intended to quantify the capacity for positive plasticity relative to the individual baseline performance.

In FIG. 3A are a sequence of four phases of the CPT-1D that are executed in the sequence shown from left to right, which generally correspond to the four phases shown and described in FIG. 1. A time vector having a scale which can be in seconds, minutes or days shows the direction of passage of time. These phases are a Baselining phase 400, an initial Plasticity Test 1 baseline phase 402 (PT1), a Cortical Excitation (iTBS) phase 404, and a Performance Test phase 406.

The Baselining phase 400 corresponds to the Baselining phase 100 in FIG. 1. The initial Plasticity Test 1 baseline phase 402 corresponds to the Pretest Calibration phase 102 of FIG. 1. The Cortical Excitation (iTBS) phase 404 corresponds to the Brain Perturbation phase 104 of FIG. 1. The Performance Test phase 406 corresponds to the Cortical Performance Testing phase 106 of FIG. 1. In the present embodiment, the Performance Test phase 406 includes 4 sub-phases following in sequence: Plasticity Test 2 sub-phase 408 (PT2), Plasticity Test 3 sub-phase 410 (PT3), Plasticity Test 4 sub-phase 412 (PT4) and Plasticity Test 5 sub-phase 414 (PT5). Where relevant, the approximate time for executing each phase and sub-phase is shown in FIG. 3A.

Now the phases and the sub-phases of FIG. 3A are now described in further detail.

In the present embodiment, the Baselining phase 400 can be the same as described for the Baselining phase 200 in FIG. 2A and is therefore not repeated here.

Following is PT1, which can be the same as described for the CT1 in FIG. 2A and is therefore not repeated here. The next step is to localize the dorsolateral prefrontal cortex (dlPFC). This is the same as step 306 of FIG. 2B, with the following small variation. In this embodiment, the localization should be completed within a 2-minute time window following the completion of the baseline cognitive task executed in PT1.

In the present embodiment, this localization step is included as part of PT1 to end the phase. Alternately, this localization step can be included as part of the following Cortical Excitation (iTBS) phase 404 to begin its phase. In either variant, the TMS coil is appropriately positioned and secured to the head of the individual.

Next is the Cortical Excitation (iTBS) phase 404. iTBS is an excitatory variant of rTMS stimulation. The TMS coil is controlled to generate the theta burst pattern, of triplet 50 Hz clusters of pulses repeating at 5 Hz, with a pattern of 2 seconds of active stimulation alternating with 8 seconds of delay. This sequence repeats for a total of 600 pulses; for a total stimulation time of 3 min 33 seconds. Alternately, the iTBS phase 404 can employ a total of 300 pulses as previously explained.

Upon completion of iTBS delivery, there is a rest period for the individual lasting 2 minutes when no test activity is applied to or required by the individual. This 2 minute rest period is shown in FIG. 3A. Once these 2 minute rest period ends, the Performance Test phase 406 begins.

As shown in FIG. 3A, the Performance Test phase 406 includes a sequential set of testing sub-phases when in each sub-phase an interference task is executed by the individual under test. The same type of task is to be executed in each sub-phase, which is the same type as the interference task executed in PT1. In this particular embodiment, there are a total of four Performance Test sub-phases: Plasticity test 2 sub-phase 408 (PT2), Plasticity test 3 sub-phase 410 (PT3), Plasticity test 4 sub-phase 412 (PT4) and Plasticity test 5 sub-phase 414 (PT5) each lasting about 5 minutes in duration to complete. Again, all of the plasticity tests are of the same type. The individual feedback response is registered and recorded, and if used, functional activity in the brain is recorded and time synchronized with presentation of a task and the individual response. It is estimated that the total time between execution of the first interference task in PT1 until the end of the last interference task in PT5 is 30 minutes.

In the presently described embodiment, the use of at least 2 sequentially occurring Plasticity Test sub-phases allows for quantification of the time course of the iTBS effect on the individual. Taking the present embodiment by example, the individual under test may respond with a peak score in PT3, but then steadily decline in PT4 and PT5. In another example, the individual may respond with a peak score in PT4, and then decline in PT5. These characteristics of the temporal response of the brain can be important for diagnosis or other clinical objective.

The Plasticity Test sub-phases are shown as being distinct, because the individual receives a slight break in between each test sub-phase in order to help reset their attention between the end of the current test and the beginning of the next test. From a user experience facet, it may even help to change the screen color to distinguish between the end of the current test and beginning of the next test to help the individual reset their attention. This differs from the embodiment of FIG. 2A where there is a distinct and substantive longer Recovery sub-phase 210 between CT2 and CT3.

The measurement of the brain response in the present CPT-1D embodiment is understood to be the change in score on each test phase/sub-phase based on feedback from the individual and/or corresponding recorded blood oxygenation level dependent (BOLD) functional brain derived from fMRI or fNIRS. The change in score and BOLD response would normally be positively correlated.

Both these brain response variables can then be compared to normative value stratified by sex and age by example, identifying a percentile score as the focal parameter (score or BOLD value) of interest. The cognitive interference task used in the CPT-2 protocol can be any interference task, but it will be understood that the version must match the version used in the normative comparison sample, in order for a valid percentile value to be derived. Persons of skill in the art will understand that other brain imaging systems can be used in combination with each other such that the data gathered complement each other to improve accuracy or to provide additional data.

In a variation to the use of a BOLD metric, electroencephalography (EEG) can be used instead to quantify brain response. This would involve quantifying an event related response parameter such as N100 or P300 (or other appropriate event-related or resting state parameter) as the neural signature associated with dlPFC engagement (or lack thereof). Additionally, a combination of both BOLD and EEG can be used. More specifically, this means that the system includes sensors to detect both BOLD and EEG signals. This can improve the system by allowing for a highly sensitive temporal signal to be detected (EEG), while preserving the spatial resolution superiority of BOLD imaging modalities mentioned (fNIRS and fMRI).

Figure 3B:
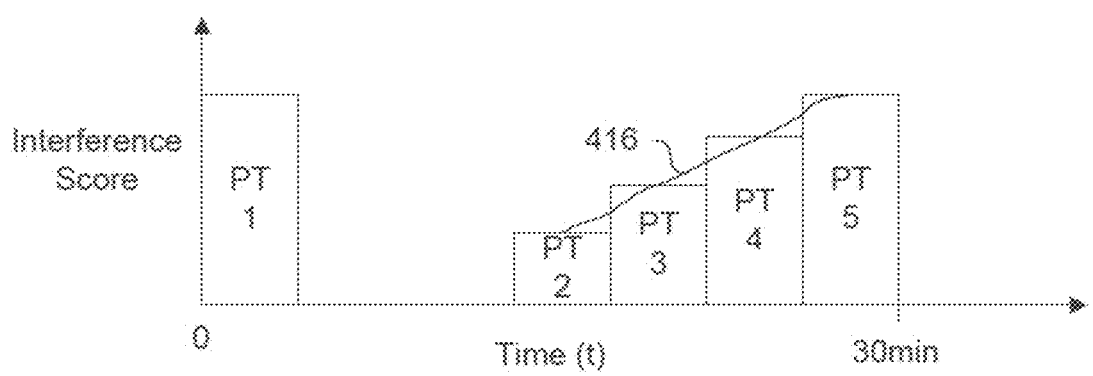
FIG. 3B is a graph plotting example quantitative test results of the test from FIG. 3A.

FIG. 3B shows example response scores for an individual undergoing the present CPT-1D method shown in FIG. 3A. The horizontal axis represents time while the vertical axis represents interference score by the individual in response to each interference task. The spacing of the horizontal axis is aligned with the horizontal timeline in FIG. 3A to better illustrate the correspondence of each testing phase/sub-phase and the respective scores in FIG. 3B. Relative to the baseline score in PT1, a lower interference score corresponds to improved functioning of the individual, while a higher interference score corresponds to a lowered or degraded functioning of the individual.

In the example of FIG. 3B, the interference score from the PT1 is now the baseline score for the individual. In PT2 which occurs 2 minutes after iTBS delivery, it can be seen that the individual has improved their interference score, which is indicative of improved cortical performance. As time progresses in this example, it can be seen that the effects of iTBS start to wear off as the scores for PT3, PT4 and PT5 progressively return towards the baseline score in PT1.

Concurrently with the execution of the tests by the individual, brain imaging is used to quantify neural response during each of PT1 to PT5, and cumulatively across each of PT1 to PT5. This could be oxyhemoglobin concentration change in fNIRS within the dlpfc, for example.

Person skilled in the art will understand that the response scores, such as the ones shown in FIG. 3B by example, can be manipulated in a variety of ways to obtain certain metrics of interest.

In one example, a peak or best task score (or average test score) between PT2-PT5 minus the baseline task score from PT1 should be calculated and expressed as a % of the baseline task score from PT1. This is the plasticity metric of interest, and can be compared to the normative database. The same process is also used to calculate functional activation parameters using the measurement from above.

Both test scores and functional activation parameters can be subjected to ROC analyses wherein area under the curve is calculated and used as the metric of interest. In particular, the time series created by continuous performance testing in each of PT2-PT5, when the mean values are connected, creates and area under the curve (see 416 in FIG. 3B). This area can be of theoretical interest, and represents the total sum of stimulation effects spread across all post-iTBS testing. This can be considered an index of how responsive overall the person is to stimulation.

Figure 4A:
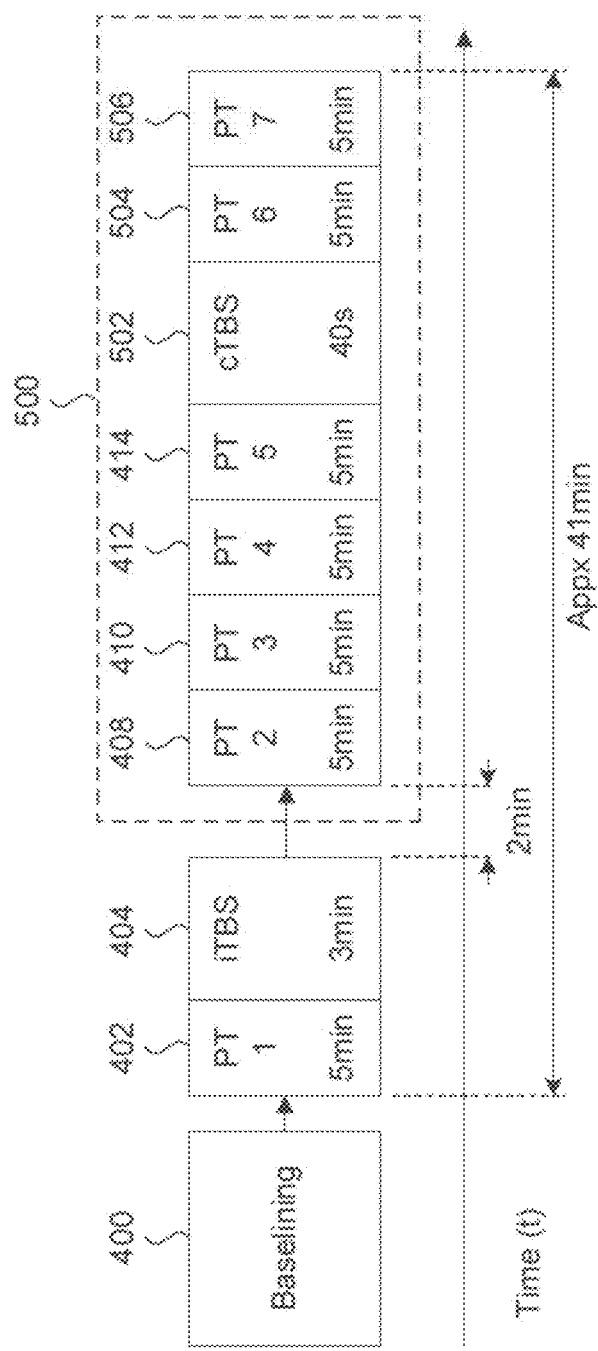
FIG. 4A is an embodiment of the method of FIG. 1 showing an alternate method for testing cortical plasticity, according to a present embodiment.

Reference is now made to FIG. 4A which is an alternate embodiment of the method of FIG. 3A showing a method embodiment for testing cortical plasticity, referred to as the Bidirectional Cortical Plasticity Test (CPT-2D). CPT-2D uses the negative and positive functional deflections from individual baseline performance to quantify the capacity for positive and negative plasticity, respectively, as well as a total representing the different between the two.

The primary difference between CPT-2D and CPT-1D is that CPT-2D includes an additional brain perturbation with additional testing at the end of CPT-1D. In FIG. 3B are a sequence of four phases of the CPT-2D that are executed in the sequence shown from left to right, which generally correspond to the four phases shown and described in FIG. 1. A time vector having a scale which can be in seconds, minutes or days shows the direction of passage of time. These phases are a Baselining phase 400, an initial Plasticity Test 1 baseline phase 402 (PT1), a Cortical Excitation (iTBS) phase 404, and a Performance Test phase 500. The elements in FIG. 4A having the same reference numerals as those in FIG. 3A are intended to be the same. Therefore no further description of these elements in FIG. 4A is needed.

The Performance Test phase 500 corresponds to the Cortical Performance Testing phase 106 of FIG. 1. In the present embodiment, the Performance Test phase 500 includes the same 4 sub-phases of FIG. 3A following in sequence: Plasticity Test 2 sub-phase 408 (PT2), Plasticity Test 3 sub-phase 410 (PT3), Plasticity Test 4 sub-phase 412 (PT4) and Plasticity Test 5 sub-phase 414 (PT5).

The additional sub-phases introduced by CPT-2D in Performance Test phase 500 include a Cortical Suppression sub-phase 502 (cTBS), followed by Plasticity Test 6 sub-phase 504 (PT6) and then by Plasticity Test 7 sub-phase 506 (PT7). As in the previously described embodiments, brain imaging can also be employed concurrently with the testing being done in PT6 and PT7. Where relevant, the approximate time for executing each phase and sub-phase is shown in FIG. 4A.

In the present embodiment, the Cortical Suppression sub-phase 502 can be the same as that described in FIG. 2A for the Cortical Suppression phase 204, where either cTBS-600 or cTBS-300 can be used. Another baselining phase similar to 400 can be executed prior to the start of the Cortical Suppression sub-phase 502. Each of PT6 and PT7 are again interference tasks similar in type to the ones in PT1-PT5. It should be understood that specific test given to the individual in each of PT1-PT7 are not identical in the detailed tasks or questions being asked, but are each still structured or configured in the same way. There is a very short break in time between PT6 and PT7, to help the individual reset their attention. In the timing example shown in FIG. 4A, the total time for administering CPT-2D after the Baselining phase 400 is about 41 minutes.

Figure 4B:
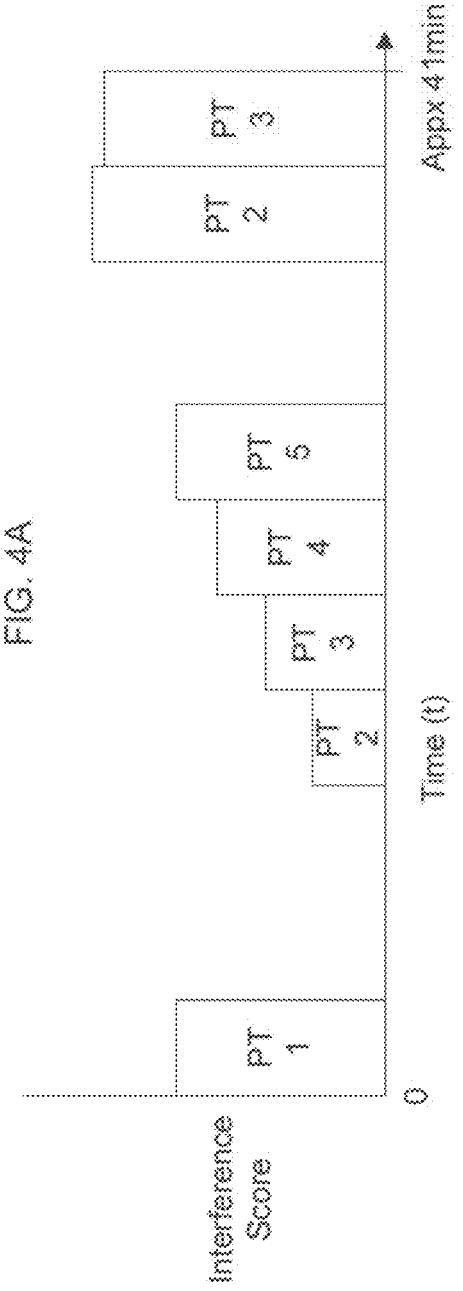
FIG. 4B is a graph plotting example quantitative test results of the test from FIG. 4A.

FIG. 4B shows example response scores for an individual undergoing the present CPT-1D method shown in FIG. 4A. The horizontal axis represents time while the vertical axis represents interference score by the individual in response to each interference task. The spacing of the horizontal axis is aligned with the horizontal timeline in FIG. 4A to better illustrate the correspondence of each testing phase/sub-phase and the respective scores in FIG. 4B. Relative to the baseline score in PT1 a lower interference score corresponds to improved functioning of the individual, while a higher interference score corresponds to a lowered or degraded functioning of the individual.

In the example of FIG. 4B, the interference score from the PT1 is now the baseline score for the individual. In PT2 which occurs 2 minutes after iTBS delivery, it can be seen that the individual has improved their interference score, which is indicative of improved cortical performance. As time progresses in this example it can be seen that the effects of iTBS start to wear off as the scores for PT3, PT4 and PT5 progressively return towards the baseline score in PT1. This is the same example as presented in FIG. 3B. In the present example of FIG. 4B, after PT5 is delivery of cTBS to the individual, which has a suppressive effect opposite to the earlier iTBS from the Cortical Excitation phase 404. In this example, due to the suppressive effect of cTBS, the individual now scores worse than baseline in PT1. Following in PT3, there is a slight decrease in the interference score meaning that the individual is progressively returning to baseline performance levels. It is also possible that the PT3 score further increases.

Consideration of the difference between the peak and trough scores, or the averages thereof can be the value of interest for CPT-2D, which would then be compared to a normative value. Again, brain imaging data can be used to complement the response scores from PT2 and PT3.

To summarize, CPT-1D and CPT-2D embodiments provide an operationalization the plasticity concept when applied to the prefrontal cortex. This can be of use as a diagnostic assessment wherein insidious reductions in cortical plasticity are the hallmark features of the early onset of a disorder, or improvements in plasticity are expected as a result of a therapeutic intervention. Likewise, the tests can be used in research contexts to examine the causal determinants of plasticity.

The previously described embodiments are not limited to PFC applications, and could also be applied to other areas of the cortex.

Figure 5:
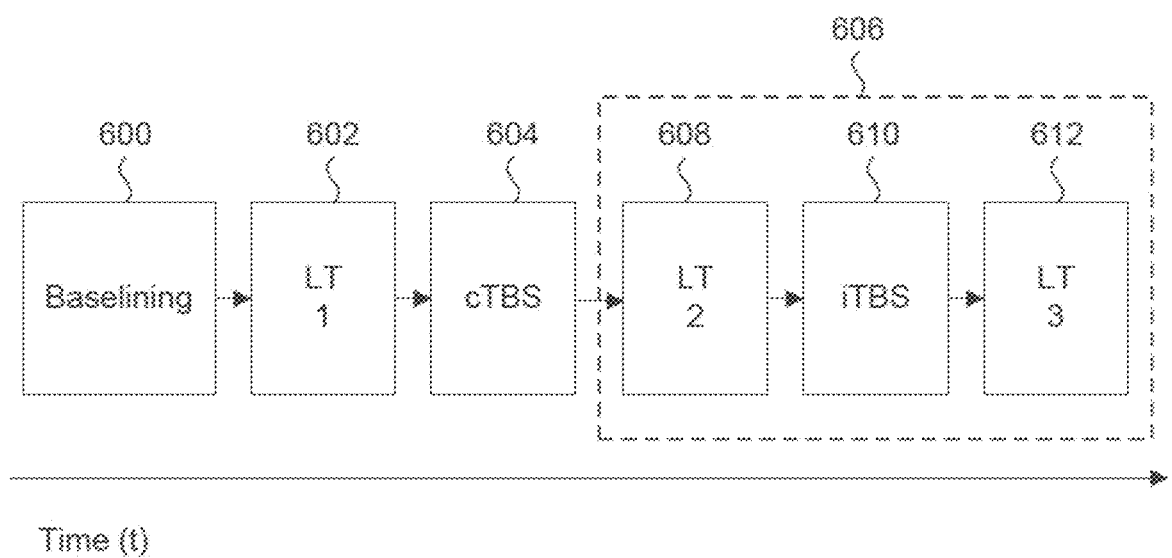
FIG. 5 is an alternate embodiment of the method of FIG. 1 showing a method for limit testing, according to a present embodiment.

Reference is now made to FIG. 5 which is an alternate embodiment of the method of FIG. 1 showing a method embodiment for limit testing of an individual. Prior to a discussion of the embodiment of FIG. 5, an explanation of limit testing is first provided.

The purpose of limit testing is to examine the upper and/or lower limits of possible performance for a given individual under maximally optimal or maximally suboptimal conditions. In standard cognitive assessment procedures, limit testing is typically done through social means, including by example, providing encouragement, or other interpersonal reinforcement during the task. Another technique for conducting limit testing is to provide additional functional support, including for example by providing a note pad for arithmetic or word problems. These prior techniques can be used to determine the upper limits of performance. Examples of determining the lower levels of performance can be done by removal of usual aids to performance, including for example by removing a response key, so that it has to be memorized by the patient. However, limit testing is often done via qualitative observation of performance, and the actual nature of the support provided is not strictly standardized. There are no systematic limit testing protocols in existence that utilize standardized enhancement or suppression of performance using neuromodulation of cortical network function.

The limit testing method embodiment of FIG. 5 is a method that uses both the previously described cTBS and iTBS delivered to an important network node of the brain, such as the dlPFC, or other cortical node, for given cognitive task. In this method, a standardized excitatory (optimal) or suppressive (sub-optimal) brain perturbation will result in an observable impact on individual performance in relation to a standard cognitive task. This will allow the upper and lower bounds of performance potentials to be realized. This upper and lower boundary to performance—identifying what is "possible" in relation to performance for a given individual—may predict outcomes and other desired objectives beyond normal task performance, particularly when, for example, and underlying disease process affecting the brain may not yet manifest in "normal" performance (i.e., early stages of dementia).

The limit testing embodiment of FIG. 5 includes a sequence of four phases that are executed in the sequence shown from left to right, which generally correspond to the four phases shown and described in FIG. 1. A time vector having a scale which can be in seconds, minutes or days shows the direction of passage of time. These phases are a Baselining phase 600, an initial Limit Test 1 baseline phase 602 (LT1), a Cortical Suppression phase 604 (cTBS), and a Performance Test phase 606.

The Baselining phase 600 corresponds to the Baselining phase 100 in FIG. 1. The initial Limit Test 1 phase 602 (LT1) corresponds to the Pretest Calibration phase 102 of FIG. 1. The Cortical Suppression phase 604 (cTBS) corresponds to the Brain Perturbation phase 104 of FIG. 1. The Performance Test phase 606 corresponds to the Cortical Performance Testing phase 106 of FIG. 1. In the present embodiment, the Performance Test phase 606 includes 3 sub-phases: a second Limit Test 2 sub-phase 608 (LT2) followed by a Cortical Excitation sub-phase 610, and a final Limit Test 3 sub-phase 612 (LT3).

The sequence of phases and sub-phases appears similar to that of FIG. 4A, except that the cortical suppression and excitation phases are reversed in position, and that there is only one test sub-phase after cTBS and only one test sub-phase after iTBS within the Performance Test phase 606. Another difference is that the timescale is no longer measured in minutes, but instead in multiples of hours. This is explained in further detail as follows.

In the present embodiment, the Baselining phase 600 can be the same as described for the Baselining phase 200 in FIG. 2A and is therefore not repeated here.

Following is LT1, in which a particular test for assessing cognitive functioning is administered to the individual. In the present embodiments, this is a digit symbol substitution test, which is part of the Wechsler Adult Intelligence Test (WAIS) and all known technique for measuring intelligent quotient (IQ) of an individual. The result is converted to a norm-referenced value (e.g., percentile), considered the baseline performance of the individual. Any standard, norm based cognitive test can be used in place of the digit symbol substitution test. LT1 is not limited to the digit symbol substitution test, which is merely one example of a test which can be administered. In alternative embodiments, LT1 can be like the previously described interference tests, like Stroop from the KDEFS battery, which is norm referenced.

Similar to the previously described embodiments, localization of the dlPFC is necessary for proper placement of the TMS coil on the head of the individual. As in the previously described embodiments, this can be included as part of LT1 or at the beginning of the Cortical Suppression phase 604.

After localization of the dlPFC, cTBS in is delivered in the Cortical Suppression phase 604 to provide a suppressive effect to the individual. In this embodiment, cTBS is delivered with the same parameters as described for the CCaRT embodiment of FIG. 2A (using cTBS-600). In a possible variant of this phase, cTBS can be delivered according to the parameters of cTBS-300 instead.

Immediately after the end of cTBS, the Performance Test phase 606 begins with LT2. This is the same type of test as in LT1. The score result by the individual in LT2 is converted to a norm-referenced value (e.g. percentile), considered the lower limit performance of the individual.

In the present embodiment, the Baselining phase 600, LT1, cTBS and LT2 are conducted within a single sitting, or occasion by the individual. Once the individual has completed the test of LT2, a recovery time having a minimum duration whereby all residual effects of cTBS have worn off is required. This should be at least 3 hours and up to 24 hours after the delivery of cTBS. Accordingly, this single sitting or first occasion ends, and the individual is permitted to leave the testing site.

Once this recovery time has ended, the individual returns for another sitting, referred to as the second occasion whereby the Performance Test phase 606 is resumed. It should be understood that the recovery time is considered part of the Performance Test phase 606.

In this second occasion, baselining similar to baselining phase 600 is conducted (not shown) prior to the Cortical Excitation sub-phase 610. Furthermore, localization of the dlPFC and placement of the TMS coil as it is assumed the coil was removed prior to the recovery time. iTBS having the same parameters as described in the CPT-1D embodiment of FIG. 3A or the CPT-2D embodiment of FIG. 4A can be used here. Particular, iTBS-600 or iTBS-300 can be used.

After the delivery of iTBS is the execution of the last test in LT3 using the same type of test as in LT1 and LT2. It should be understood that specific test given to the individual in each of LT1, LT2 and LT3 are not identical in the detailed tasks or questions being asked, but are each still structured or configured in the same way.

Completion of LT3 ends the performance test phase 606 and the limit testing method. This resulting score from LT3 is converted to a norm-referenced value, and is considered the upper limit performance of the individual.

Accordingly, the limit testing embodiment described above provides a systematic method and protocol for determining quantitative values corresponding to the upper and lower limits of performance for an individual.

The previously described method embodiments have introduced some of the components required for execution of certain aspects of the method. Following is a more fulsome description of an example hardware system which can be employed for the previously described method embodiments.

Figure 6:
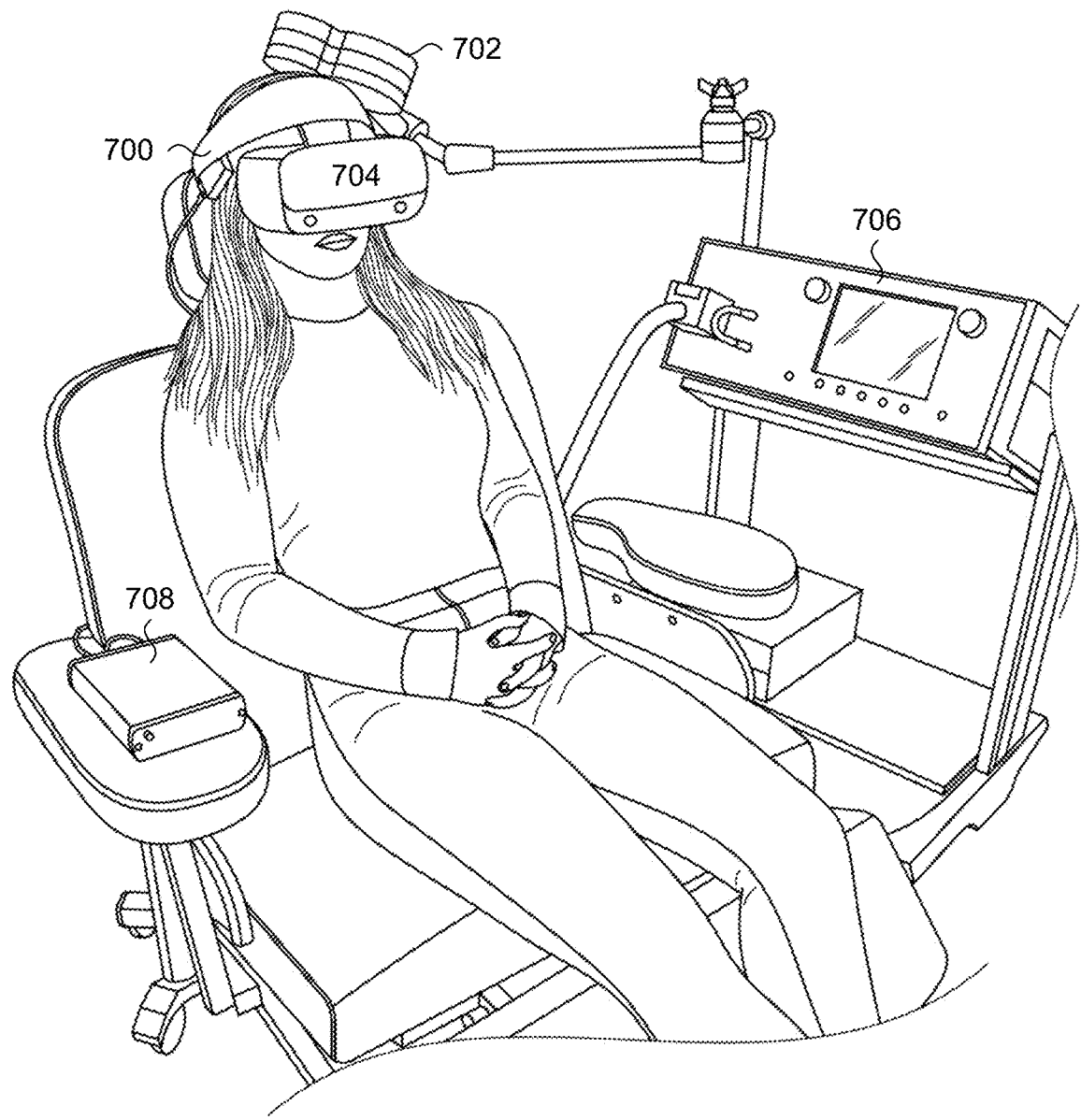
FIG. 6 is a picture showing a system for executing the previously described methods, according to a present embodiment.

All the previously described method embodiments can be executed with the hardware system embodiment shown in FIG. 6. FIG. 6 is a picture showing an individual seated in a chair with various components necessary for execution of the method embodiments.

The system of FIG. 6 includes an fNIRS sensor band 700, an rTMS coil 702, virtual reality goggles 704, an rTMS device 706, an fNIRS console 708, and a computer (not shown). The sensor band 700 is configured for placement over the head of an individual, and includes multiple light sources and sensors embedded therein facing the head surface. The coil 702 is secured adjacent to the sensor band 700, and can be moved for specific placement over an area of the head surface, as guided by dlPFC localization procedures mentioned previously. The coil can also be moved for specific placement proximate the motor cortex to conduct the previously described physiological baselining.

The virtual reality goggles 704 are used for presentation of the cognitive task stimulus and can also be connected to the sensor band 700. Alternately, the virtual reality goggles 704 can be replaced with a simple computer screen or tablet for presenting the cognitive testing stimuli. A benefit of the virtual reality goggles 704 is that the individual is less likely to be distracted by their surroundings.

The rTMS coil 702 is connected to the rTMS device 706, which is configurable to provide cTBS or iTBS. It is noted that the rTMS device 706 and cortical response measurement (cog. testing+brain imaging) are controlled by the computer (not shown), such that cortical response measurements and perturbation (cTBS stimulation targeting the dlPFC) are delivered in a precise time-locked manner in accordance with the previously described methods.

The computer is also programmed, as an executable application, to process the response measurements. By example, for the CCaRT embodiment of FIG. 2A, such software running on the computer cleans, refines, and combines the time-lagged cortical response measures and calculates a cortical resilience metric in raw score form (% of perturbation effect recovered at CT3) and compares to normative values, producing a percentile value as well as the raw score for interpretation.

The fNIRS console 708 is connected to the fNIRS sensor band 700 to control the emitters and sensors, and to provide an interface to the computer (not shown) in order to provide imaging data. In the presently shown system, the virtual reality goggles 704 are functionally integrated with the fNIRS sensors, which can be controlled by the computer, to standardize delivery of the cognitive task and quantify continuous changes in lateral PFC oxygenation prior to and following cTBS stimulation targeting the dlPFC, in synchronization with the presented tasks.

Various forms of brain imaging could be substituted for the fNIRS system in order to measure various indicators of functional brain response. Once again turning to the CCaRT embodiment of FIG. 2A, EEG can be used to measure various indicators of functional brain response during execution of CT1, CT2 and CT3. EEG electrodes arranged in accordance with the international 10-20 system, for instance, could be employed to quantify neuroelectric indices of brain activity, and use subtraction to identify the initial suppressive effect of cTBS followed by the recapture of function in the follow up interval. Finally, several types of rTMS stimulator coil could deliver the stimulation, including a miniaturized version for use in an fMRI scanner, if fMRI is being used as the imaging modality.

Not shown in FIG. 6 is a response actuator, such as a button device or keyboard, for actuation by the individual in response to the task presented in the virtual reality goggles 704. This actuator would also be connected to the computer (not shown) to receive and record responses actuated by the individual.

A significant shortcoming of the hardware set up shown in FIG. 6 is the TMS coil positioning that is required. As it was described in the previous method embodiments, there is a baselining phase in which the coil is positioned on one part of the head to stimulate the motor cortex. Then later the coil is repositioned to a different part of the head to deliver the cTBS or iTBS to the dlPFC. Naturally there are ideal positions for the coil to ensure maximal efficiency and delivery of the magnetic fields to the intended target area in the brain.

Neuronavigation systems are available, and are basically non-invasive computer-assisted technologies to help practitioners locate structures of the brain to facilitate targeting of particular structures for rTMS. However these systems are expensive and due to the cost, many private practicing TMS clinicians and researchers make use of assistants for daily TMS session delivery instead. Unfortunately such assistants often have minimal technical training for positioning the TMS coil properly, and instead may need to rely on manual measurement of stimulation targets on a cap with a marker in combination with trial and error.

According to another embodiment of the present invention, a device is provided which is low cost and simple to use which facilitates the positioning of the TMS coil for use with the previously described method embodiments of FIGS. 2A, 2B, 3A, 4A and 5.

Figure 7A:
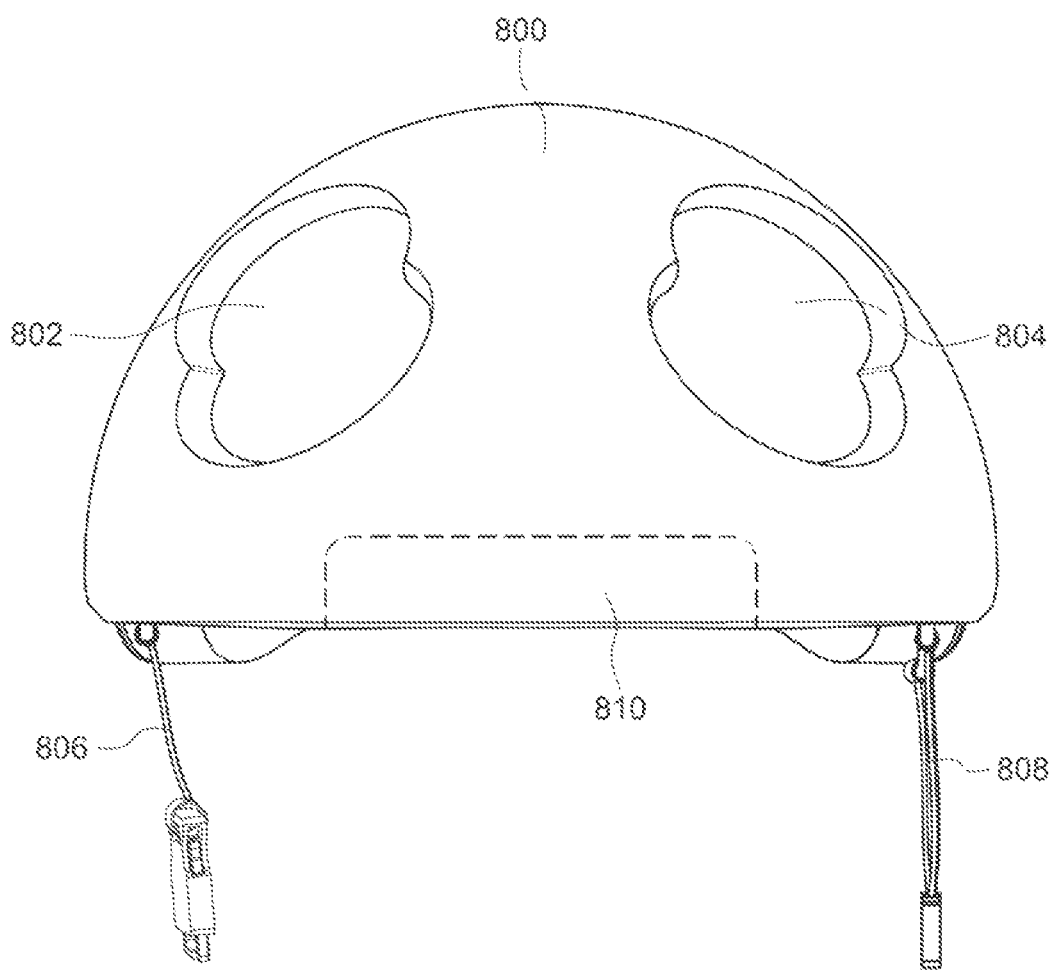
FIG. 7A shows a front view of a helmet with pre-positioned locations for transcranial magnetic stimulation (TMS) coils and sensors.
Figure 7B:
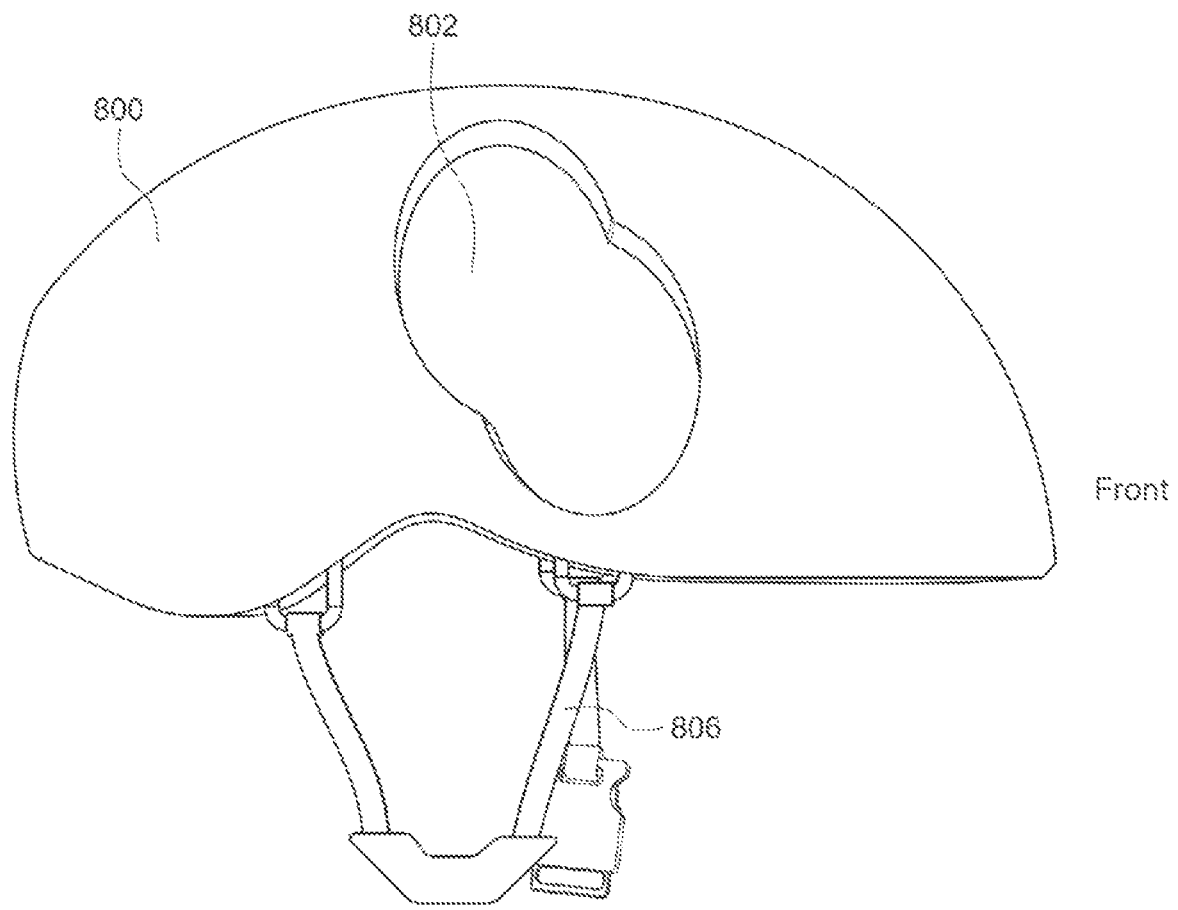
FIG. 7B shows a right side view of the helmet of FIG. 7A.
Figure 7C:
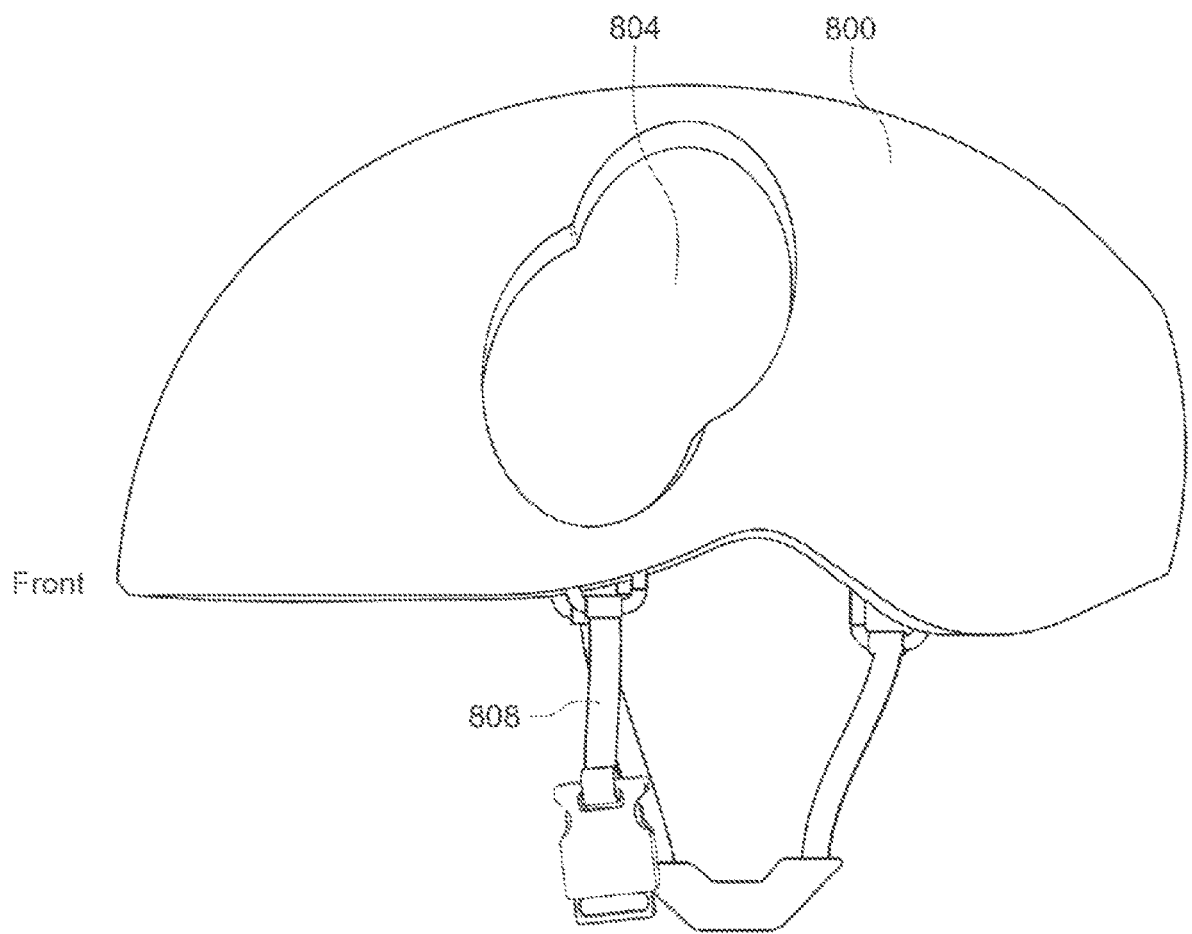
FIG. 7C shows a left side view of the helmet of FIG. 7A.
Figure 7D:
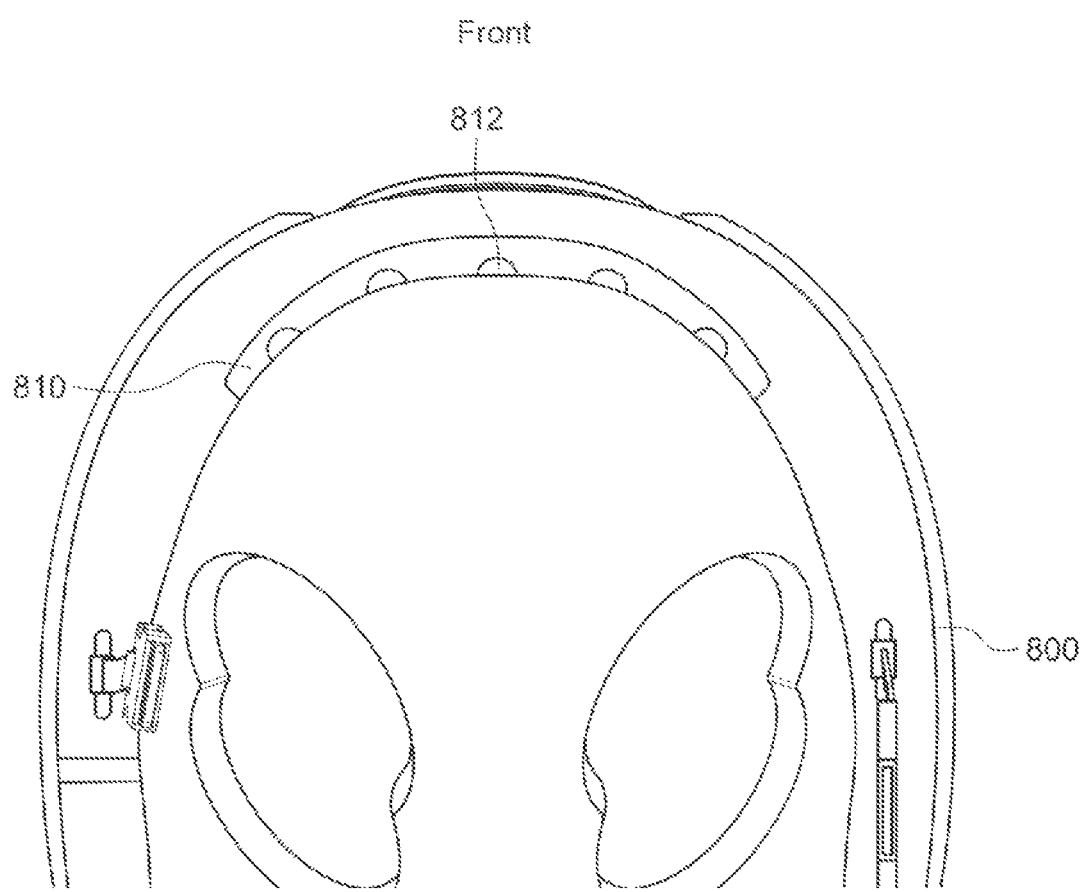
FIG. 7D shows an underside view of the helmet of FIG. 7A.

FIGS. 7A, 7B, 7C and 7D are illustrations of a fitted helmet apparatus with precision cut TMS coil guides for easy insertion and removal of the TMS coil. FIG. 7A is a front view of the helmet. FIG. 7B shows a right side view of the helmet. FIG. 7C shows a left side view of the helmet. FIG. 7D shows an underside view of the helmet.

In one embodiment, the helmet 800 is designed to fit like a conventional bicycle helmet, having an interior adjustable basket with pads to provide a fine fit over the head. Accordingly, the helmet 800 can come in large, medium and small coarse sizes based on average head shape and size for adults. Another set of large, medium and small helmet sizes can be designed for youths. As would be understood by persons of skill in the art, the interior of the helmet is concave while the exterior of the helmet is convex in shape.

The front view shown in FIG. 7A shows all the relevant features of the helmet 800, according to the present embodiment. The helmet 800 has a body which can be made of polystyrene with a plastic outer shell, similar to a sports helmet. The helmet 800 includes a right side TMS coil guide cut out 802, and a left side TMS coil guide cut out 804. A partial view of right side strap 806 and left side strap 808 are shown extending from the bottom side of helmet 800. Shown in dashed lines near the front of the helmet 800 is a sensor array area 810, in the form of a sensor band in the present embodiment. This sensor band is positioned on the inner surface of the helmet 800. In the present embodiment the sensor array includes fNIRS sensors for tracking brain response to treatment. Depending on the type of brain imaging system being used the sensor array area 810 may be in a different area of the helmet 800 and may include the appropriate sensor technology for the system being used.

FIG. 7B is the right side view of helmet 800 clearly showing the right side TMS coil guide cut out 802. The cut out 802 is precision cut to match a specific brand and model of coil. The cutout is generally all the way through from outer surface to bottom inner surface of the helmet, with retaining tabs or an inner lip/flange that extends into the opening from the inner surface side to prevent the inserted TMS coil from falling through. The angular orientation of the cutout 802 is preset.

The straps 806 can be configured in any way such that once the helmet is positioned on the head of an individual, it can be releasably attachable to the opposite side strap 808 (not shown) via buckles or other similar attachment means under the chin of the head, and then tightened to minimize random movement of the helmet on the head. In this configuration the inserted TMS coil is accurately positioned proximate to the motor cortex and in the proper orientation to direct the generated magnetic waves so that the baselining phases 100, 200, 400 and 600 can be executed quickly.

FIG. 7C is the left side view of helmet 800 clearly showing the left side TMS coil guide cut out 804. Typically the same TMS coil is used, therefore the cutout 804 is precision cut to match the same specific brand and model of coil as for cut out 802. Alternately, a different cutout matching a different coil brand or model can be made if 2 different TMS coils are concurrently inserted in both cutouts 802 and 804. Regardless, once the TMS coil is inserted into cutout 804, it is accurately positioned proximate to the dIPFC and in the proper orientation to direct the generated magnetic waves for brain perturbation such as the cTBS and iTBS described for various phases and sub-phases of the prior cortical resilience, plasticity and limit testing method embodiments.

While the presently described embodiment is specific to an orientation and position of the TMS coil cut out 804 suitable for targeting the dIPFC, other brain structures can be targeted with corresponding change in the position and orientation of the cutout 804. For example, the cutout 804 can be positioned and oriented to target the superior parietal lobule.

FIG. 7D is a partial underside view of helmet 800 with the front side of the helmet pointing towards the top of the page. This view shows the sensor array area 810, where an fNIRS sensor band can be positioned with its embedded light emitters 812. The sensor array is not limited to the position shown in figures, and any number of sensor array areas can be used and placed anywhere in the underside of the helmet 800.

While an fNIRS based system is described for integration in helmet 800, such a system can be replaced by different brain imaging system. Alternately, multiple imaging systems can be integrated into the helmet to provide complementary data during execution of the previously described embodiments.

While not shown, it should be understood to persons skilled in the art that wired or wireless communication means are provided between the sensor band and an fNIRS console, such as console 708 in the hardware setup shown in FIG. 5. In fact, many of the components shown in FIG. 5 can be used in conjunction with helmet 800.

Use of this helmet 800 will greatly streamline the coil positioning process, which is of substantial interest among practicing clinicians currently using TMS in the clinical environment.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

The invention claimed is:

1. A method for diagnosing and assessing at least one of cortical resilience and loss of cortical plasticity of a human individual, comprising:

executing by the human individual in a pre-test phase, a baseline cognitive interference task consisting of multiple individual trials to determine a baseline performance parameter value for the individual, wherein an electronic system records actuations of an interface device by the human individual in response to the multiple individual trials;

in a brain perturbation phase after the pre-test phase, delivering brain stimulation at a calibrated level to the dorsolateral prefrontal cortex (dIPFC) or other cortical target of the human individual by controlling a transcranial magnetic stimulation (TMS) coil that generates magnetic waves for changing a state of the brain to an artificially induced state, wherein the pre-test phase and the brain perturbation phase are executed in a single sitting by the human individual;

stopping the delivery of brain stimulation;

executing by the human individual in a cortical performance testing phase after the brain perturbation phase and after delivery of brain stimulation is stopped, at least a first cognitive interference task consisting of multiple individual trials of the same type as the baseline cognitive interference task, a recovery period for the human individual after completion of the first cognitive interference task, and a second cognitive interference task consisting of multiple individual trials of the same type as the baseline cognitive interference task prior to the end of the recovery period, wherein the electronic system records actuations of the interface device by the human individual in response to the multiple individual trials of the at least first and second cognitive interference tasks, to determine by the electronic system at least once performance parameter value for the individual to complete the at least first and second cognitive interference tasks, wherein the at least one performance parameter value and the baseline performance parameter value are of the same type; and comparing each of the at least one performance parameter value to the baseline performance parameter value by the electronic system to provide at least one metric compared to a normative database for outputting the level of cortical resilience and/or loss of cortical plasticity of the human individual.

2. The method of claim 1, further including generating images of the brain with neuroimaging apparatus positioned on a head of the human individual, while the human individual executes the baseline cognitive interference task, and while the human individual executes each of the at least first and second cognitive interference tasks.

3. The method of claim 1, wherein the calibrated level is determined in a calibration phase executed before the baseline cognitive interference task, and includes calibrating a TMS stimulation intensity level for the individual.

4. The method of claim 3, wherein calibrating the TMS stimulation intensity level includes
determining a resting or active motor TMS threshold level for the human individual, and
setting the calibrated TMS stimulation intensity level between 70% and 120% of the resting motor TMS threshold level.

5. The method of claim 1, wherein delivering brain stimulation includes controlling the TMS coil to deliver a magnetic field pulsed at a preset frequency, duration and magnitude corresponding to the calibrated TMS stimulation intensity level.

6. The method of claim 5, wherein the preset frequency, duration and magnitude are set to change the state of the brain into a suppressed state.

7. The method of claim 5, wherein the preset frequency, duration and magnitude are set to change the state of the brain into an excitatory state.

8. The method of claim 6, wherein the TMS coil is controlled to deliver 600 pulses of stimulation continuously in a theta burst pattern including clusters of three 50 Hz pulses, repeated at 5 Hz.

9. The method of claim 8, wherein
the first cognitive interference task is executed 5 minutes after delivery of the brain stimulation has ended,
the recovery period ends 40 minutes after delivery of the brain stimulation has ended, and
the second cognitive interference task is executed near the end of the recovery period.

10. The method of claim 6, wherein the TMS coil is controlled to deliver at least 300 pulses of stimulation continuously in a theta burst pattern including clusters of three 50 Hz pulses, repeated at 5 Hz.

11. The method of claim 10, wherein
the first cognitive interference task is executed after delivery of the brain stimulation has ended,
the recovery period ends 20 minutes after delivery of the brain stimulation has ended, and
the second cognitive interference task is executed near the end of the recovery period.

12. The method of claim 7, wherein in the cortical performance testing phase, the at least first and second cognitive interference tasks includes
at least two plasticity tests executed in sequence and indicating a transition between each test to the human individual, where the at least two plasticity tests and the baseline cognitive interference task are cognitive tests of the same type.

13. The method of claim 12, wherein indicating the transition includes at least one of a minimally timed break and providing a visual indication of the transition.

14. The method of claim 12, wherein the cortical performance testing phase further includes
controlling the TMS coil to deliver a pulsed magnetic field to the dlPFC of the human individual to change the state of the brain into a suppressed state after execution of a last plasticity test by the human individual,
executing by the human individual at least two further plasticity tests in sequence with a minimally timed break therebetween after completed delivery of the magnetic field, where the at least two further fifth plasticity tests are cognitive tests of the same type as the at least two plasticity tests.

15. The method of claim 12, wherein the TMS coil is controlled to deliver 600 pulses of stimulation continuously in a theta burst pattern including triplet 50 Hz clusters of pulses repeating at 5 Hz, with a pattern of 2 seconds of active stimulation alternating with 8 seconds of delay.

16. The method of claim 12, wherein the TMS coil is controlled to deliver 300 pulses of stimulation continuously in a theta burst pattern including triplet 50 Hz clusters of pulses repeating at 5 Hz, with a pattern of 2 seconds of active stimulation alternating with 8 seconds of delay.

17. The method of claim 6, wherein in the cortical performance testing phase, the at least first and second cognitive interference tasks includes
executing by the human individual a first limit test,
controlling the TMS coil to deliver a magnetic field to the dlPFC of the human individual to change the state of the brain into an excitatory state after completion of the first limit test by the human individual, and
executing by the human individual a second limit test after completed delivery of the magnetic field, where the first limit test, the second limit test and the baseline cognitive interference task are cognitive tests of the same type.

18. The method of claim 17, wherein
the TMS coil is controlled to deliver the magnetic field to change the state of the brain into an excitatory state any time between 3 hours and 24 hours after completion of the first limit test by the human individual.

* * * * *